(12) United States Patent
Piszczek et al.

(10) Patent No.: US 11,572,325 B2
(45) Date of Patent: Feb. 7, 2023

(54) PROCESS FOR THE SEPARATION OF LINEAR ALPHA-OLEFINS USING A DIVIDING WALL COLUMN

(71) Applicants: Robert Piszczek, Spring, TX (US); Brian W. Heins, Humble, TX (US); Paul Hamilton, Hampshire (GB); Terrance C. Osby, Spring, TX (US); Dion Zhang, Houston, TX (US); Zhongcheng Wang, Spring, TX (US); Michael L. Hergenrother, Kingwood, TX (US); Jason A. Nichols, Houston, TX (US)

(72) Inventors: Robert Piszczek, Spring, TX (US); Brian W. Heins, Humble, TX (US); Paul Hamilton, Hampshire (GB); Terrance C. Osby, Spring, TX (US); Dion Zhang, Houston, TX (US); Zhongcheng Wang, Spring, TX (US); Michael L. Hergenrother, Kingwood, TX (US); Jason A. Nichols, Houston, TX (US)

(73) Assignee: ExxonMobil Chemical Patents Inc., Baytown, TX (US)

( * ) Notice: Subject to any disclaimer, the term of this patent is extended or adjusted under 35 U.S.C. 154(b) by 0 days.

(21) Appl. No.: 17/297,408

(22) PCT Filed: Nov. 14, 2019

(86) PCT No.: PCT/EP2019/081275
§ 371 (c)(1),
(2) Date: May 26, 2021

(87) PCT Pub. No.: WO2020/114744
PCT Pub. Date: Jun. 11, 2020

(65) Prior Publication Data
US 2022/0033327 A1    Feb. 3, 2022

Related U.S. Application Data

(60) Provisional application No. 62/774,958, filed on Dec. 4, 2018.

(30) Foreign Application Priority Data

Feb. 19, 2019  (EP) .................................... 19158087

(51) Int. Cl.
C07C 7/04        (2006.01)
B01D 3/14        (2006.01)
(Continued)

(52) U.S. Cl.
CPC ................ C07C 7/04 (2013.01); B01D 3/141 (2013.01); B01D 3/143 (2013.01); B01D 3/40 (2013.01); C07C 7/005 (2013.01)

(58) Field of Classification Search
CPC .......... B01D 3/141; B01D 3/143; B01D 3/40; C07C 7/005; C07C 7/04
See application file for complete search history.

(56) References Cited

U.S. PATENT DOCUMENTS 6,291,734 B1 * 9/2001 Stork ....................... C10G 7/00
                                                   585/809
7,169,267 B2 * 1/2007 Kaibel .................... C10G 7/12
                                                   203/99
(Continued)

FOREIGN PATENT DOCUMENTS

WO       2017/115305 A1    7/2017
WO   WO-2017115305 A1 *    7/2017
WO       2018/208375 A1   11/2018

OTHER PUBLICATIONS

U.S. Appl. No. 62/564,505.

*Primary Examiner* — Jonathan Miller
(74) *Attorney, Agent, or Firm* — ExxonMobil Chemical Patents Inc.

(57) ABSTRACT

Many linear alpha olefin (LAO) syntheses form a range of LAO products when oligomerizing ethylene in the presence of a Ziegler-type catalyst. The range of products typically
(Continued)

requires a plurality of distillation columns to separate the LAO products up to a desired carbon count, but such approaches may be energy- and capital-intensive. LAO product separation using at least one dividing wall column may lessen these burdens. Methods for separating LAOs may comprise: providing a pre-processed product stream comprising C8+ linear alpha olefins (LAOs) to a first of a series of distillation columns, at least one member of the series of distillation columns comprising a dividing wall column; and separating an overhead stream comprising a first LAO from the dividing wall column and one or more side streams from the dividing wall column, each side stream comprising a different LAO that also differs from the first LAO.

29 Claims, 16 Drawing Sheets

(51) Int. Cl.
  *B01D 3/40* (2006.01)
  *C07C 7/00* (2006.01)

(56) References Cited

U.S. PATENT DOCUMENTS

| | | | |
|---|---|---|---|
| 10,918,967 B2 | 2/2021 | Piszczek | |
| 11,052,324 B2* | 7/2021 | Piszczek | B01D 3/143 |
| 2005/0252761 A1* | 11/2005 | Funke | B01D 3/146 |
| | | | 203/99 |
| 2007/0185362 A1* | 8/2007 | Lattner | C07C 2/36 |
| | | | 585/521 |
| 2019/0091600 A1* | 3/2019 | Piszczek | B01D 3/141 |
| 2020/0062672 A1* | 2/2020 | Weber | C08F 10/00 |
| 2020/0087229 A1* | 3/2020 | Piszczek | C10G 7/12 |
| 2022/0033327 A1* | 2/2022 | Piszczek | B01D 3/143 |

* cited by examiner

PROCESS FOR THE SEPARATION OF LINEAR ALPHA-OLEFINS USING A DIVIDING WALL COLUMN

CROSS-REFERENCE TO RELATED APPLICATIONS

This application is a National Phase Application claiming priority to PCT Application Serial No. PCT/EP2019/081275 filed Nov. 14, 2019, entitled PROCESS FOR THE SEPARATION OF LINEAR ALPHA-OLEFINS USING A DIVIDING WALL COLUMN which claims the benefit of U.S. Provisional Patent Application 62/774,958, filed on 4 Dec. 2018, entitled METHODS FOR SEPARATING LINEAR ALPHA OLEFINS USING A DIVIDING WALL COLUMN, and European Patent Application Number 19158087.7, filed on 19 Feb. 2019, entitled METHODS FOR SEPARATING LINEAR ALPHA OLEFINS USING A DIVIDING WALL COLUMN, the disclosures of which are incorporated by reference herein in their entireties.

FIELD

The present disclosure relates to linear alpha olefin (LAO) syntheses.

BACKGROUND

Linear alpha olefins (LAOs), which also may be referred to as linear alpha alkenes, linear terminal olefins, linear terminal alkenes, or normal alpha olefins are a commercially valuable class of chemical compounds. Polymerization is the primary market for LAOs, in which they are most frequently used as a co-monomer during copolymerization of ethylene. Another significant market for LAOs is as a precursor for linear aldehydes and carboxylic acids formed through oxidation, as a precursor for higher olefins, or as a precursor for linear internal olefins (LIOs) formed through double bond isomerization. LAOs are also sometimes directly incorporated in drilling fluids, surfactants, lubricants, and detergents, for example.

LAOs may be synthesized by several different processes starting from low molecular weight feedstock materials. The primary route for synthesizing LAOs is via ethylene oligomerization, of which there are several synthetic variants that may be mediated using different Ziegler-type catalysts. Depending on the particular Ziegler-type catalyst and the synthetic conditions, ethylene oligomerization reactions may form a range of homologous LAOs having an even number of carbon atoms (i.e., $C_{2n}H_{2n}$, where n is a positive integer greater than or equal to 2), or a predominant LAO (e.g., 1-butene, 1-hexene, 1-octene, or 1-decene) may be produced. When multiple LAOs are formed, the product distribution of the LAOs may follow a Shulz-Flory distribution, with the distribution being arranged about a central molecular weight. Such processes are commonly referred to as full-range or wide-range LAO synthesis processes.

Fractional distillation processes are frequently employed to separate LAO product streams into desired fractions comprising individual or multiple LAOs. Typical distillation processes for separating LAOs from one another may employ a two-product distillation column to isolate an overhead stream comprising an individual LAO or LAO mixture and then passing a bottoms stream on to a subsequent distillation column for isolating another individual LAO or LAO mixture. This process is iterated until LAOs up to a desired carbon count have been separated from one another. Given that a distribution of LAOs may be formed in LAO syntheses, a commercial plant having a large footprint may result from the need to employ separate distillation columns for each LAO or LAO mixture being fractionated. Moreover, distillation columns are expensive plant components, both from a capital expenditure standpoint and operationally (i.e., energy usage), thereby significantly impacting the cost of LAOs obtained through ethylene oligomerization. Associated ancillary components such as reflux drums, condensers, reboilers, pumps, piping, control valves, instrumentation, civils (foundations), insulation, fireproofing, and the like may also present significant cost considerations.

SUMMARY

In various embodiments, the present disclosure provides methods for separating LAOs. The methods comprise: providing a pre-processed product stream comprising $C_{8+}$ linear alpha olefins (LAOs) to a first of a series of distillation columns, at least one member of the series of distillation columns comprising a dividing wall column; and separating an overhead stream comprising a first LAO from the dividing wall column and one or more side streams from the dividing wall column, each side stream comprising a different LAO that also differs from the first LAO.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, as will occur to one of ordinary skill in the art and having the benefit of this disclosure.

In FIG. 9, the dual dividing wall column is configured to separate three side streams therefrom, and in FIG. 10 the dual dividing wall column is configured to separate four side streams therefrom.

DETAILED DESCRIPTION

Figure 1A:
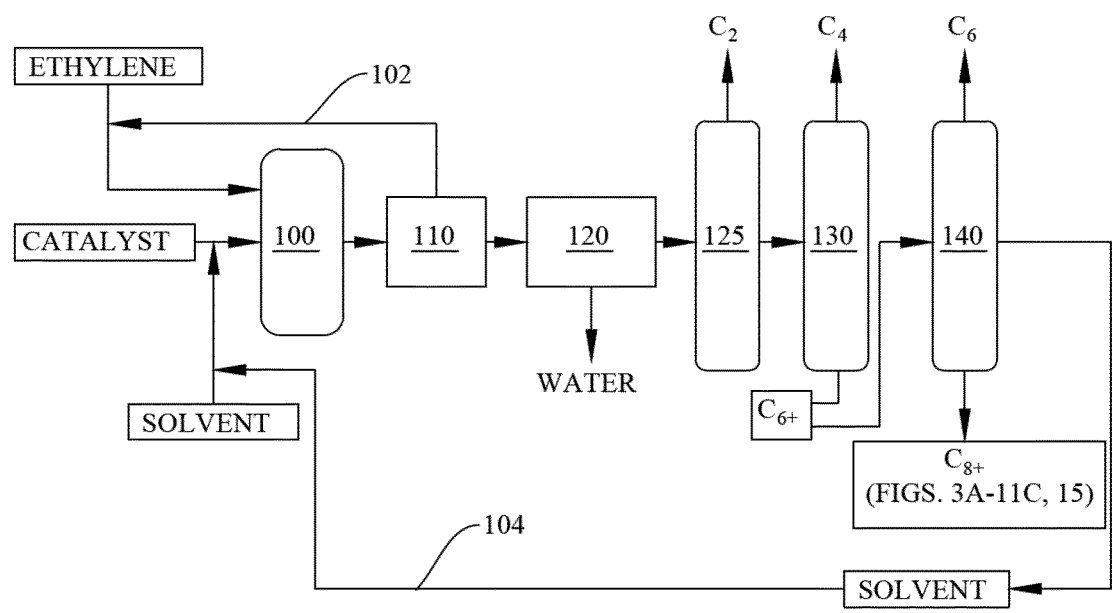
FIGS. 1A-1D show block diagrams illustrating various operations that may be performed in the course of forming and isolating LAOs, and which may be implemented with one or more embodiments of the present disclosure.

The present disclosure generally relates to linear alpha olefins and, more specifically, to methods for separating linear alpha olefins using at least one dividing wall column.

As discussed above, linear alpha olefins (LAOs) are often obtained as a range of ethylene oligomers having a terminal double bond and an even-numbered carbon count. Such LAOs are typically separated using multiple distillation columns arranged in series, with each distillation column providing a single LAO or LAO mixture as the column's overhead stream. Thus, for each LAO or LAO mixture obtained, a corresponding number of distillation columns are present in a 1:1 ratio. Such separation approaches may lead to a large plant footprint on an industrial scale, in addition to significant energy costs and capital expenditure. In some cases, the value of a given LAO may not be sufficient to justify the expense of incorporating a distillation column needed to achieve its separation, particularly for a LAO that is present in low abundance.

The present disclosure describes how one or more dividing wall columns may be utilized to improve the efficiency of separating individual LAOs or LAO mixtures from one another. Dividing wall columns, the basic operational principles and various configurations of which are described below, may be utilized to separate multiple components from one another upon a single distillation column. As used herein, the term "dividing wall column" refers to a distillation column featuring one or more dividing walls (partitions) that separate an interior space of the column into at least a first chamber and a second chamber. The term "dividing wall column" encompasses both dividing wall columns having a single wall dividing wall and multiple dividing walls, the latter of which may be referred to herein as "dual dividing wall columns." The one or more dividing walls may be vertical or sloped with respect to a true vertical configuration. When using a dividing wall column, lighter molecular weight (lower boiling point) components may be separated as an overhead stream and heavier (higher boiling point) components may be separated as a side stream (if desired) or retained as a bottoms stream. Dividing wall columns featuring a single dividing wall may provide a single side stream or multiple side streams (e.g., an upper side stream for components that volatilize over the dividing wall and a lower side stream for components that volatilize under the dividing wall), whereas dual dividing wall columns may provide multiple side streams, each side stream providing a distinct LAO composition. Depending on the interior configuration of a given dual dividing wall column, up to four distinct side streams may be obtained, as described in commonly owned U.S. Provisional Patent Application 62/564,505, which is incorporated herein by reference in its entirety. As such, utilizing at least one dividing wall column to separate LAOs into desired fractions may decrease the number of distillation columns needed to affect separation compared to distillation configurations featuring only two-product distillation columns. Thus, utilizing one or more dividing wall columns to promote LAO separation may provide advantageous capital expenditure savings and reduced operating costs.

In addition to the foregoing advantages offered by dividing wall columns, they may be particularly well suited for separating homologous LAOs from one another. In a homologous series of LAOs, each two-carbon increase in the LAO chain length increases the boiling point by about 60° C. The wide boiling point separation between homologous LAOs makes these entities well adapted for separation using a dividing wall column approach. Namely, the wide boiling point separation may facilitate ready separation of an LAO overhead stream from one or more heavier LAO side streams. Similarly, multiple LAO side streams may be readily separable from one another due to the wide boiling point separation.

Thus, the distillation configurations of the present disclosure may provide significant advantages over those presently employed for separating LAOs. More specifically, distillation configurations of the present disclosure employing at least one dividing wall column in a series of distillation columns may afford isolated LAO fractions ranging from $C_8$ LAOs up to about $C_{18}$, $C_{20}$, $C_{22}$ or $C_{24}$ LAOs, depending on configuration. Combined LAO product streams may be obtained in some cases (e.g., $C_{16}/C_{18}$, $C_{18}/C_{20}$, $C_{18}$-$C_{22}$, and similar combined product streams). Even heavier LAO fractions (i.e., $C_{22+}$, $C_{24+}$ or $C_{26+}$ LAOs) may be retained as a bottoms stream from the terminal distillation column within the distillation column series, and the heavier LAOs in the bottoms stream may undergo separation by alternative techniques such as fractional solidification, differential solubility, chromatography, or the like. Depending on the desired range of LAO products to be obtained by distillation, various distillation configurations employing at least one dividing wall column may be used, as described further hereinbelow. Mixtures of heavier LAOs may also be produced according to the disclosure herein.

Still further advantages that may be afforded by utilizing at least one dividing wall column according to the present disclosure may include a decreased amount of time spent under the extreme heating conditions of a distillation column reboiler. Decreased time in the reboiler may improve product quality and yield, since a decreased propensity toward cracking and formation of color bodies may be realized. In addition, a decreased propensity toward oxygenate formation may be realized. Decreased oxygenate formation may particularly be realized when a distillation system is operated at sub-atmospheric pressures, during which time there may be an increased potential for air leakage into one or more of the distillation columns.

All numerical values within the detailed description and the claims herein are modified by "about" or "approximately" with respect to the indicated value, and take into account experimental error and variations that would be expected by a person having ordinary skill in the art. Unless otherwise indicated, room temperature is about 25° C.

As used in the present disclosure and claims, the singular forms "a," "an," and "the" include plural forms unless the context clearly dictates otherwise.

The term "and/or" as used in a phrase such as "A and/or B" herein is intended to include "A and B," "A or B," "A", and "B."

For the purposes of the present disclosure, the new numbering scheme for groups of the Periodic Table is used. In said numbering scheme, the groups (columns) are numbered sequentially from left to right from 1 through 18, excluding the f-block elements (lanthanides and actinides).

The term "hydrocarbon" refers to a class of compounds containing hydrogen bound to carbon, and encompasses (i) saturated hydrocarbon compounds, (ii) unsaturated hydrocarbon compounds, and (iii) mixtures of hydrocarbon compounds (saturated and/or unsaturated), including mixtures of hydrocarbon compounds having different numbers of carbon atoms. The term "$C_n$," refers to hydrocarbon(s) or a hydrocarbyl group having n carbon atom(s) per molecule or group along the main carbon chain, wherein n is a positive integer. Such hydrocarbon or hydrocarbyl groups may be one or more of linear, branched, cyclic, acyclic, saturated, unsaturated, aliphatic, or aromatic.

The terms "hydrocarbyl" and "hydrocarbyl group" are used interchangeably herein. The term "hydrocarbyl group" refers to any $C_1$-$C_{100}$ hydrocarbon group bearing at least one unfilled valence position when removed from a parent compound. "Hydrocarbyl groups" may be optionally substituted, in which the term "optionally substituted" refers to replacement of at least one hydrogen atom or at least one carbon atom with a heteroatom or heteroatom functional group. Heteroatoms may include, but are not limited to, B, O, N, S, P, F, Cl, Br, I, Si, Pb, Ge, Sn, As, Sb, Se, and Te. Hydrocarbyl groups therefore may include alkyl, alkenyl, alkynyl, aryl, heteroaryl, cycloalkyl, heterocyclyl, and the like, any of which may be optionally-substituted.

The term "alkyl" refers to a hydrocarbyl group having no unsaturated carbon-carbon bonds, and which may be optionally substituted. The term "alkyl" may be used synonymously with the term "paraffinic."

The term "alkenyl" refers to a hydrocarbyl group having a carbon-carbon double bond, and which may be optionally substituted. The terms "alkene" and "olefin" are used synonymously herein. Similarly, the terms "alkenic" and "olefinic" are used synonymously herein. Unless otherwise noted, all possible geometric isomers are encompassed by these terms.

The terms "aromatic" and "aromatic hydrocarbon" refer to a hydrocarbon or hydrocarbyl group having a cyclic arrangement of conjugated pi-electrons that satisfy the Hückel rule. The terms "aryl" and "aromatic" may be used synonymously herein. The term "aryl" refers to both aromatic compounds and heteroaromatic compounds, either of which may be optionally substituted. Both mononuclear and polynuclear aromatic compounds are encompassed by these terms.

The terms "linear" and "linear hydrocarbon" refer to a hydrocarbon or hydrocarbyl group having a continuous carbon chain without side chain branching.

The term "linear alpha olefin (LAO)" refers to an alkenic hydrocarbon bearing a carbon-carbon double bond at a terminal (end) carbon atom of the main carbon chain.

The terms "branch," "branched" and "branched hydrocarbon" refer to a hydrocarbon or hydrocarbyl group having a linear main carbon chain in which a hydrocarbyl side chain extends from the linear main carbon chain.

The terms "unbranched" and "normal" synonymously refer to a straight-chain hydrocarbon or hydrocarbyl group.

The term "higher LAO" refers to LAOs having at least 6 carbon atoms.

The term "light olefin" refers to olefins having 5 carbon atoms or less, especially ethylene and 1-butene ($C_4$ LAOs).

The term "individual LAO" refers to a distillation fraction consisting essentially of a single LAO, particularly about 95% or greater of a single LAO by weight.

The term "two-product distillation column" refers to any distillation column that is not a dividing wall column. Two-product distillation columns typically provide an overhead stream and a bottoms stream unless specific provisions are made to withdraw a side stream. Unless expressly referred to as being another type of distillation column (e.g., a dividing wall column), it is to be understood that any distillation column of unspecified type in the present disclosure is a two-product distillation column.

The terms "terminal" and "terminus" refer to the most downstream of a series of distillation columns.

The term "direct fluid communication sequence" refers to an output, particularly a bottoms stream, from a first distillation column being provided directly as a feed to a second distillation column.

Before providing further description of suitable process conditions and catalysts for forming LAOs, illustrative LAO syntheses will be described schematically in additional detail with reference to FIGS. 1A-1D. FIGS. 1A-1D show block diagrams illustrating various operations that may be performed in the course of forming and isolating LAOs, and which may be implemented with one or more embodiments of the present disclosure. Process details directed to obtaining individual LAOs or mixtures of LAOs using at least one dividing wall column in a series of distillation columns are provided below in reference to subsequent FIGS. 2A-15. It is to be appreciated that various features in the FIGS. may be shown in general terms and/or be described in brief in order to focus more succinctly on the LAO separation aspects of the present disclosure referenced above. For example, it is to be understood that components such as reboilers, pumps, coolant lines, and like equipment are not shown in the FIGS. in order to focus more succinctly on the separation aspects of the present disclosure, but it is to be understood that such components may be present and implemented in any suitable fashion in a physical system, as will be appreciated by one having ordinary skill in the art.

Figure 1B:
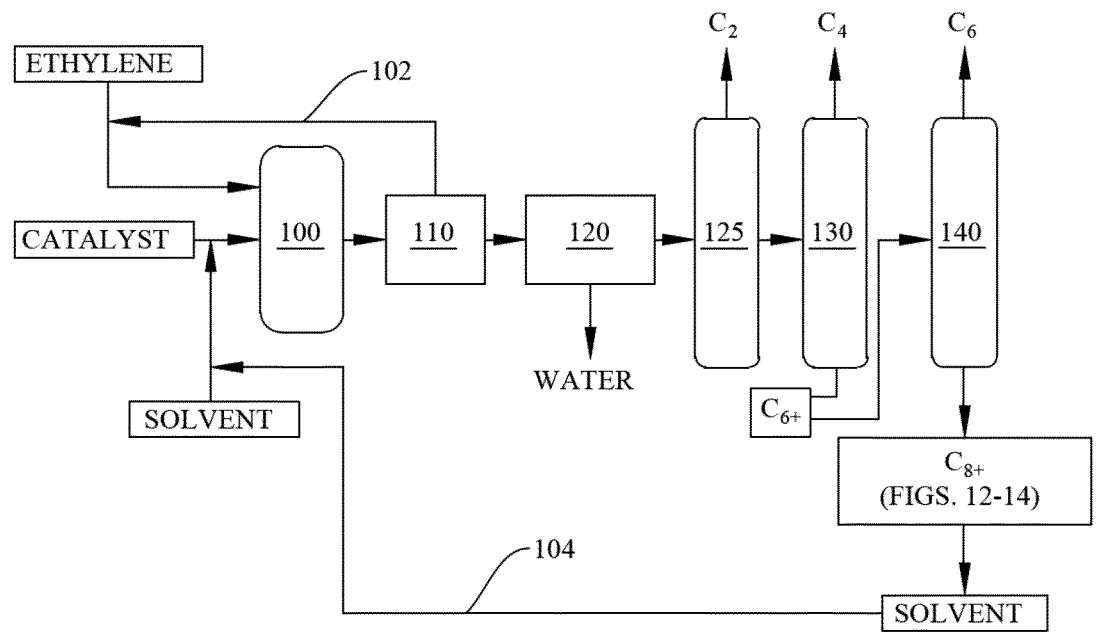

As shown in FIG. 1A, ethylene, catalyst and solvent are provided to reactor 100 via corresponding supply lines to form LAOs therein. At least a portion of the ethylene and the solvent may be recycled and provided by ethylene recycle stream 102 and recycled solvent stream 104, respectively. Ethylene recycle stream 102 and/or recycled solvent stream 104 may pass through one or more driers (not shown in FIG. 1A) prior to returning the ethylene or solvent to reactor 100. The product stream from reactor 100 next passes to ethylene recovery unit 110, whereupon some or all of the ethylene is removed from the product stream as an overhead stream and is returned to reactor 100 via ethylene recycle line 102. The product stream then proceeds from ethylene recovery unit 110 to catalyst deactivation unit 120, wherein catalyst deactivation occurs and any water used in or formed in the course of catalyst deactivation is removed. Remaining traces of ethylene and other inert hydrocarbons (e.g., methane and ethane byproducts) in the product stream may optionally be removed in lead distillation column 125. The $C_4$ LAOs formed during the LAO synthesis (i.e., 1-butene) are next removed from the product stream in an overhead stream from light olefin distillation column 130, thereby providing a higher LAO-enriched stream as a bottoms stream. The higher LAO-enriched stream comprises $C_{6+}$ LAOs and solvent. The higher LAO-enriched stream is then provided to distillation column 140 to remove $C_6$ LAOs as an overhead stream and $C_{8+}$ LAOs as a bottoms stream. Provided that the solvent has a boiling point between that of 1-hexene and 1-octene, the solvent may be removed as a side stream from distillation column 140, as shown in FIG. 1A. If the solvent has a higher boiling point, such as between the boiling points of 1-octene and 1-decene, the solvent may be removed downstream while separating the $C_{8+}$ LAOs from one another, as shown in FIG. 1B. Alternately, if a side stream comprising solvent is not removed from distillation column 140, the solvent may be separated downstream in a similar manner to that proposed in FIG. 1B. Illustrative configurations for solvent separation from $C_{8+}$ LAOs are shown below in FIGS. 12-14, which show illustrative locations at which a solvent having a boiling point between that of 1-octene and 1-decene may be collected. A solvent having a boiling point between that of 1-hexene and 1-octene may be collected downstream at a different position than that depicted in FIGS. 12-14, namely within an overhead stream obtained from the first distillation column downstream. In any of the process configurations, the $C_{8+}$ LAOs constitute a pre-processed product stream that may undergo further separation according to the disclosure herein. Namely, multiple distillation columns linked in fluid communication sequence with one another may be used to fractionate the pre-processed product stream into individual LAOs or mixtures of LAOs, as described further hereinbelow in reference to FIGS. 2A-15.

Figure 1C:
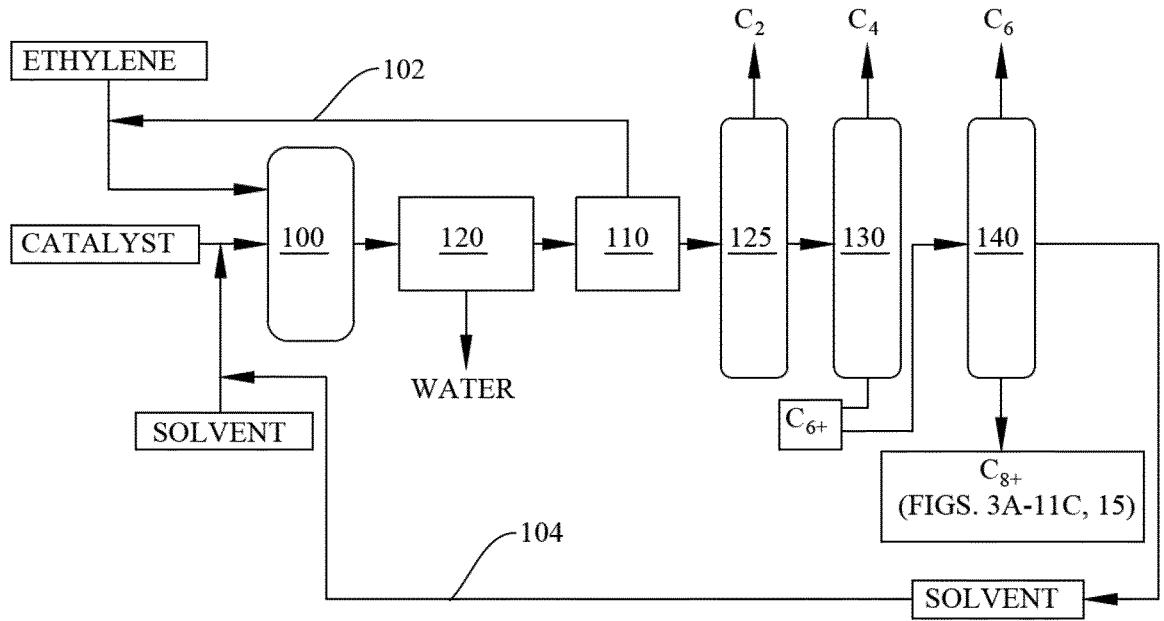
Figure 1D:
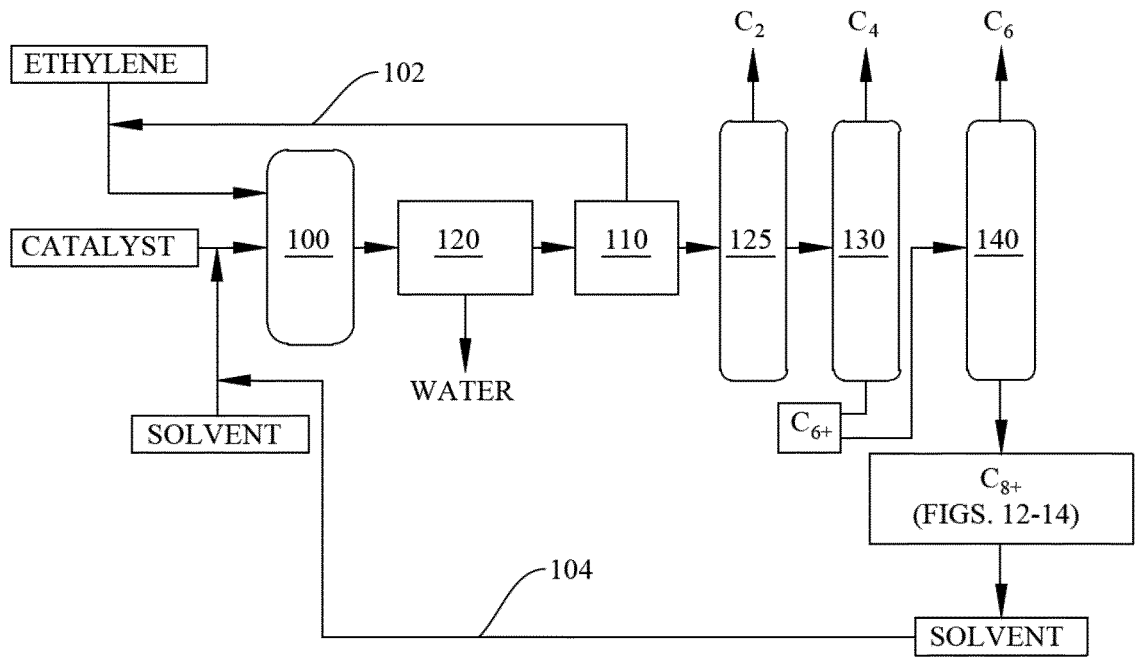

In process variations also compatible with the present disclosure, catalyst deactivation may precede ethylene recovery, as shown in FIGS. 1C and 1D. FIGS. 1C and 1D correspond to FIGS. 1A and 1B, respectively, with earlier catalyst deactivation. When catalyst deactivation precedes ethylene recovery, there may be less need for further ethylene removal using lead distillation column 125. However, further ethylene removal may take place, if desired or warranted under particular process conditions. Hence, lead distillation column 125 may be optionally omitted in such process configurations.

Ethylene may be provided to reactor 100 as a substantially pure ethylene feed or as a mixture of ethylene with one or more inert gases, such as nitrogen, helium or argon. Methane, ethane and other saturated hydrocarbon gases are also suitably inert in the LAO synthesis processes of the present disclosure and may also be present in the ethylene provided to reactor 100. The methane and ethane may be present in commercially sourced ethylene, for example. Ethylene obtained from ethylene recycle stream 102 may contain substantially pure ethylene or substantially pure ethylene and a limited amount of $C_{3+}$ alkenes, including $C_{4+}$ LAOs (e.g., <0.1 wt. % $C_{4+}$ LAOs), and/or inert gases.

Oligomerization reaction conditions suitable for synthesizing LAOs in reactor 100 may further include temperature and pressure conditions such as a temperature from about 50° C. to about 250° C. (e.g., about 170° C.), and a pressure from about 3450 kPa to about 34500 kPa or a pressure from about 6900 kPa to about 24100 kPa. In some embodiments, the temperature and pressure may be such that the ethylene is in a supercritical state, in which case the Ziegler-type catalyst and solvent may be homogenously mixed with the ethylene. The ratio of solvent to ethylene entering the reactor may range from about 0.2:1 to about 3.0:1 or about 0.5:1 to about 1.5:1, with equal volumes of solvent and ethylene being used in some embodiments.

Reactor configurations suitable for synthesizing LAOs according to the disclosure herein are not considered to be particularly limited. Suitable reactor configurations may include, for example, a fluidized bed, an ebullated bed, a slurry bed, a trickle bed, a plug flow reactor, a stirred tank reactor, a turbulent flow reactor, or any other reactor type suitable for forming a product stream. A residence time within the reactor may range between about 5 minutes to about 90 minutes, or about 5 minutes to about 15 minutes, or about 10 minutes to about 60 minutes, or about 20 minutes to about 80 minutes. Furthermore, because linearity of the alpha olefins tends to decrease with increasing carbon chain length and increasing ethylene conversion, the amount of ethylene converted during each transit through the reactor may range between about 50% to about 80%, such as from about 55% to about 70%, or from about 60% to about 65%. The conversion rate is commonly called the "per pass conversion."

Suitable solvents for forming LAOs using Ziegler-type catalysts may include various hydrocarbon solvents. Illustrative solvents that may be used when synthesizing LAOs include, for example, mineral oil; straight or branched-chain hydrocarbons (e.g., propane, isobutane, butane, pentane, isopentane, hexane, isohexane, heptane, isoheptane, octane, dodecane, 2,2-dimethylpentane, and 2,2,4-trimethylpentane); cyclic and alicyclic hydrocarbons (e.g., cyclohexane, cycloheptane, cyclooctane, methylcyclopentane; methylcyclohexane, and methylcycloheptane); perhalogenated hydrocarbons such as perfluorinated $C_4$-$C_{10}$ alkanes; aromatic hydrocarbons (e.g., benzene, toluene, ethylbenzene, mesitylene, p-xylene, m-xylene, o-xylene, chorobenzenes), and any combination thereof. Additional considerations for selecting a suitable solvent may be dictated by the location where solvent separation takes place, in which case the boiling point of the selected solvent may be taken into consideration. In illustrative embodiments, the solvent may have a boiling point ranging between that of 1-hexene and 1-octene, or between that of 1-octene and 1-decene.

Suitable Ziegler-type catalysts may include zirconium-, titanium-, magnesium-, or chromium based-catalysts. The catalyst quantity used during LAO syntheses is conveniently expressed by the weight ratio of ethylene feed to the metal in the catalyst (e.g., Ti, Mg, Zr or Cr). LAO syntheses may, according to various embodiments, be conducted at an ethylene-to-metal weight ratio ranging between about 10000:1 to about 120000:1 or between about 25000:1 to about 35000:1.

Some Ziegler-type catalysts may comprise homogeneous, single-site chromium catalysts. Such catalysts may be formed from a chromium source in combination with a heterocyclic, di-aryl, or phosphorus compound such as a pyrrole, pyridyl or pyridyl-phosphino compound, along with an aluminum activator such as methyl alumoxane (MAO) or modified methyl alumoxane (MMAO). Such catalysts may be pre-formed when provided to the reactor, or they may be formulated on-the-fly (inline) by combining the catalyst components in the supply line feeding the catalyst to the reactor.

Some Ziegler-type catalysts suitable for forming LAOs may be two-component zirconium-based catalysts. In more specific embodiments, the first component may be an adduct of a zirconium halide (i.e., $ZrCl_aBr_b$, wherein each of a and b is 0, 1, 2, 3 or 4 and a+b=4) with an organic compound having up to about 30 carbon atoms and that is selected from the group consisting of esters, ketones, ethers, amines, nitriles, anhydrides, acid chlorides, amides and aldehydes, and second component may be an alkylaluminum or alkylzinc compound selected from the group consisting of $R_2AlX$, $RAlX_2/R_3Al_2X_3$, $R_3Al$, and $R_2Zn$, in which R is a $C_1$-$C_{20}$ alkyl group and X is Cl or Br. The zirconium halide adduct (first component) may include a mole ratio of the organic compound to zirconium ranging between about 0.9:1 to about 2:1. In such embodiments, the oligomerization reaction may be conducted in the presence of about 10-50 ppm of oxygen relative to the amount of ethylene that is present. Such catalysts may likewise be pre-formed when provided to the reactor, or they may be formulated on-the-fly (inline) by combining the catalyst components in the supply line feeding the catalyst to the reactor.

In more particular embodiments of such zirconium-based Ziegler-type catalysts, the organic compound may be an ester having a formula of $R^1COOR^2$, wherein $R^1$ and $R^2$ are each $C_1$-$C_{30}$ alkyl, aryl, alkaryl, or aralkyl groups, with the proviso that $R^1$ may also be hydrogen. $R^1$ and $R^2$ taken together may also represent a cycloaliphatic group and the ester may be a lactone such as γ-butyrolactone or a phthalide. In more particular embodiments, alkyl esters having about 6 to about 16 carbon atoms may be desirable, such as n-hexyl acetate, n-heptyl acetate, n-octyl acetate, n-nonyl acetate, n-decyl acetate, isohexyl acetate, isodecyl acetate and the like, which may form dimeric equimolar adducts with $ZrCl_4$ and exhibit high catalyst solubility in common solvents suitable for forming LAOs.

When using a zirconium-based Ziegler-type catalyst for LAO syntheses, the relative amounts of the first component to the second component may vary over a wide range. In some embodiments, a mole ratio of the second component to the first component may range between about 1:1 and about 50:1 or from about 10:1 to about 25:1.

Catalyst deactivation within the product stream may take place with a suitable quenching agent, such as a caustic material in a water solution. Suitable quenching agents may include aqueous ammonia, or aqueous alkali metal or alkaline earth metal basic solutions, such as alkali metal or alkaline earth metal hydroxides, oxides, carbonates or bicarbonates. Amine quenching agents (e.g., methylamine, ethylamine, propylamine, butylamine, pentylamine, hexylamine, cyclohexylamine, octylamine, decylamine, aniline, benzylamine, naphthylamine, dimethylamine, diethylamine, dibutylamine, diphenylamine, methylphenylamine, trimethylamine, triethylamine, tributylamine, triphenylamine, pyridine, picoline, or 1,5-diamino-2-methylpentane) may be used in other embodiments. Alcohols, carboxylic acids, and phenols may also comprise suitable quenching agents in still other embodiments.

As referenced in brief above, distillation configurations and methods of the present disclosure may utilize one or more dividing wall columns to promote fractionation of a pre-processed product stream comprising mixture of $C_{8+}$ LAOs. In various embodiments, distillation methods of the present disclosure may comprise: providing a pre-processed product stream comprising $C_{8+}$ linear alpha olefins (LAOs) to a first of a series of distillation columns, at least one member of the series of distillation columns comprising a dividing wall column, and separating an overhead stream comprising a first LAO from the dividing wall column and one or more side streams from the dividing wall column, each side stream comprising a different LAO that also differs from the first LAO.

In some embodiments, the pre-processed product stream may be substantially free of solvent, such as in the pre-processed product stream formed in accordance with FIG. 1A or 1C. In other embodiments, the pre-processed product stream may comprise both LAOs and solvent, such as in the pre-processed product stream formed in accordance with FIG. 1B or 1D.

In some embodiments, the series of distillation columns may comprise at least one two-product distillation column and at least one divided wall column in combination. Two-product distillation columns suitable for use in the present disclosure are not considered to be particularly limited. The interior of the two-product distillation column may contain any combination of a plurality of distillation plates, structured corrugated metal packing, or randomly positioned loose packing materials.

A single dividing wall defines two (horizontal) chambers within a dividing wall column. Multiple dividing walls may also be present in a dividing wall column of the present disclosure to define an additional chamber and thereby promote even more effective product separation. Dividing wall columns having at least two dividing walls therein may be referred to as "dual dividing wall columns" herein. The chambers defined within a dividing wall column may contain any combination of a plurality of distillation plates, structured corrugated metal packing, or randomly positioned loose packing materials. The vertical position of the dividing wall(s) within the dividing wall column may be such that one or more side streams are obtained, if desired, from the dividing wall column at a desired column height.

The vertical and horizontal positioning of the multiple dividing walls may be adjusted to promote a desired separation of LAOs. Considerations for the vertical positioning of the multiple dividing walls may be dictated by the distillation column height needed to accomplish a desired type of separation. For example, in the case of dividing wall column 400 (FIG. 8A), the left-hand dividing wall 201 may be positioned so that $C_{10}$ LAOs travel over the wall and minimal $C_{12}$ LAOs travel or drop below the left-hand dividing wall 201. Similarly, the right-hand dividing wall 201 may be positioned such that $C_{12}$ LAOs travel over the wall and minimal $C_{14}$ LAOs travel over the wall or under the right-hand dividing wall 201. Horizontal positioning of the multiple dividing walls may be set by the relative vapor load provided to each horizontal section of the distillation column, such that a calculated pressure drop across each horizontal section is substantially equal.

A feed stream is provided to a dividing wall column at a location below the top and above the bottom of the dividing wall. The feed stream undergoes separation in the chamber it enters, but it is blocked from directly entering the chamber opposite the point of entry, thereby improving separation efficiency. Instead, an overhead stream may be obtained from the entering chamber, and the column bottoms are therefore lean in the component(s) removed in the overhead stream. Upon volatilizing the column bottoms, the vapor phase in the chamber opposite the point of feed stream entry is also lean in the component(s) removed in the overhead stream, thereby allowing a side stream to be obtained in a relatively pure state.

Figure 10:
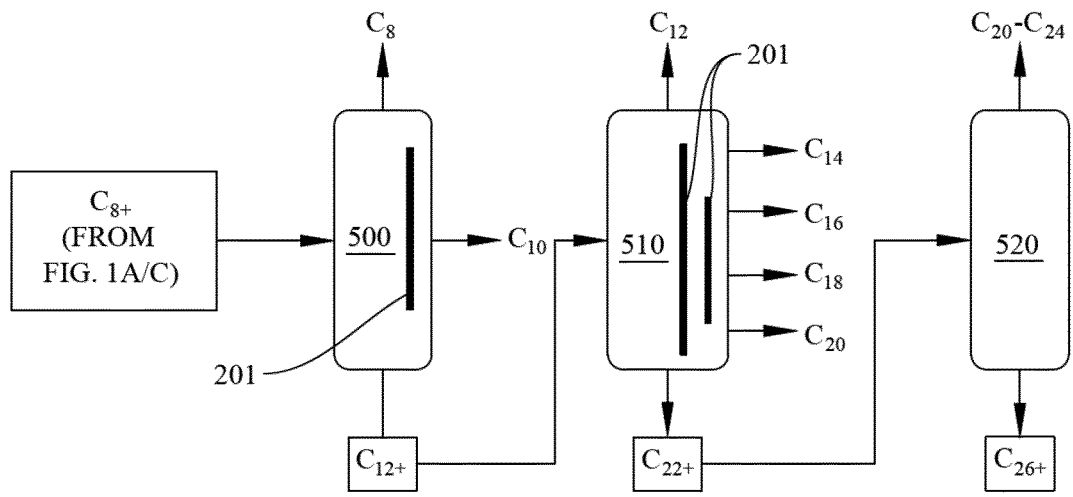
Figure 11A:
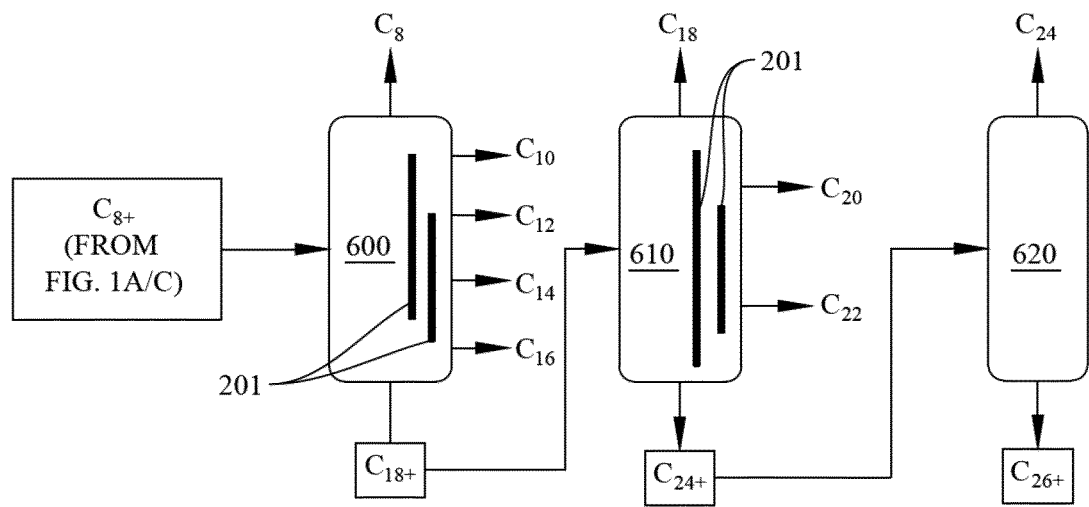
FIGS. 11A-11C show illustrative embodiments of a fifth distillation column configuration of the present disclosure that includes first and second dual dividing wall columns, and which is capable of separating individual LAO fractions up to at least $C_{20}$ LAOs when provided with a pre-processed product stream comprising $C_{8+}$ LAOs. The distillation column configurations of FIGS. 11A-11C include a series of distillation columns having a first dual dividing wall column as a first member of the series, a second dual dividing wall column as a second member of the series, and a two-product distillation column as a third member of the series.
Figure 11B:
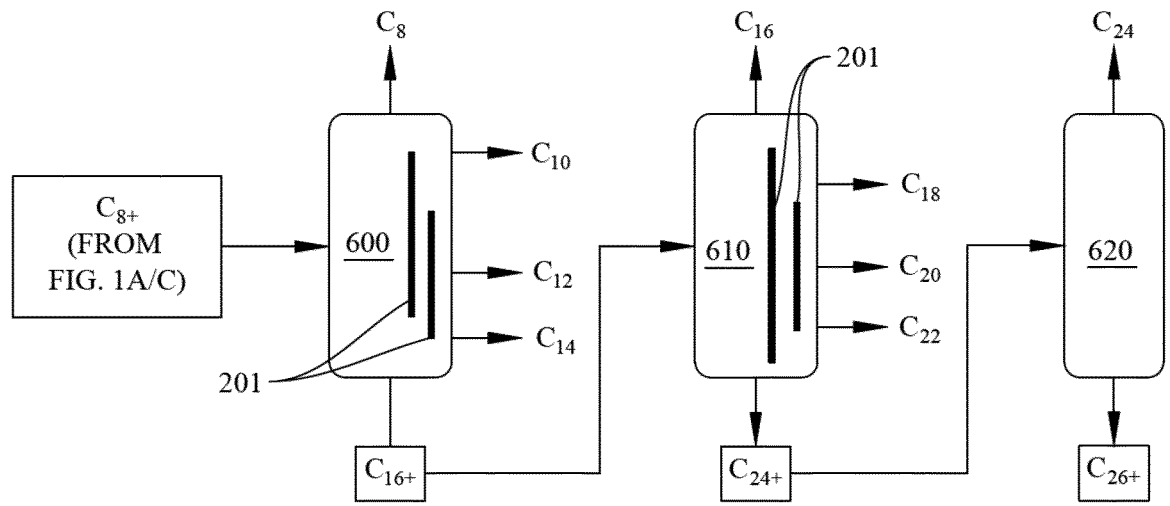
Figure 11C:
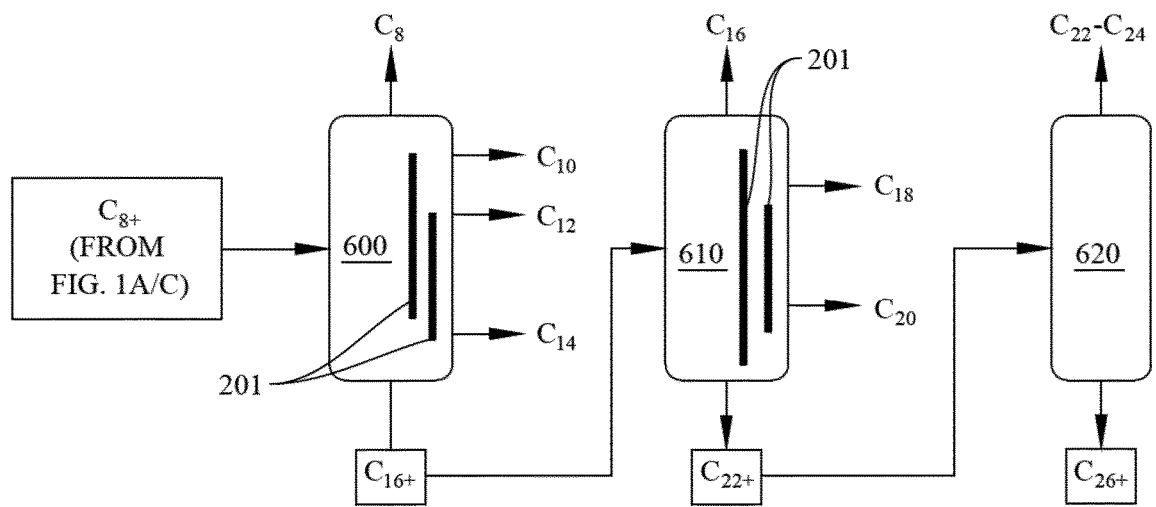
Figure 12:
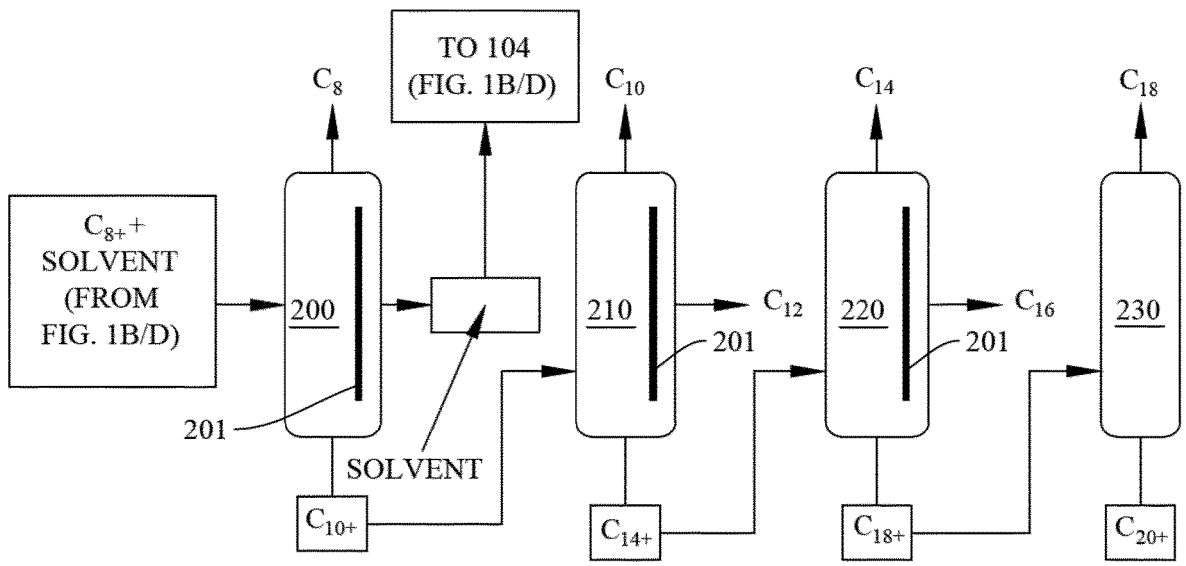
FIG. 12 shows a modified LAO separation sequence using the first distillation column configuration from FIG. 3A, in which a solvent is separated downstream from $C_6$ LAOs.
Figure 13:
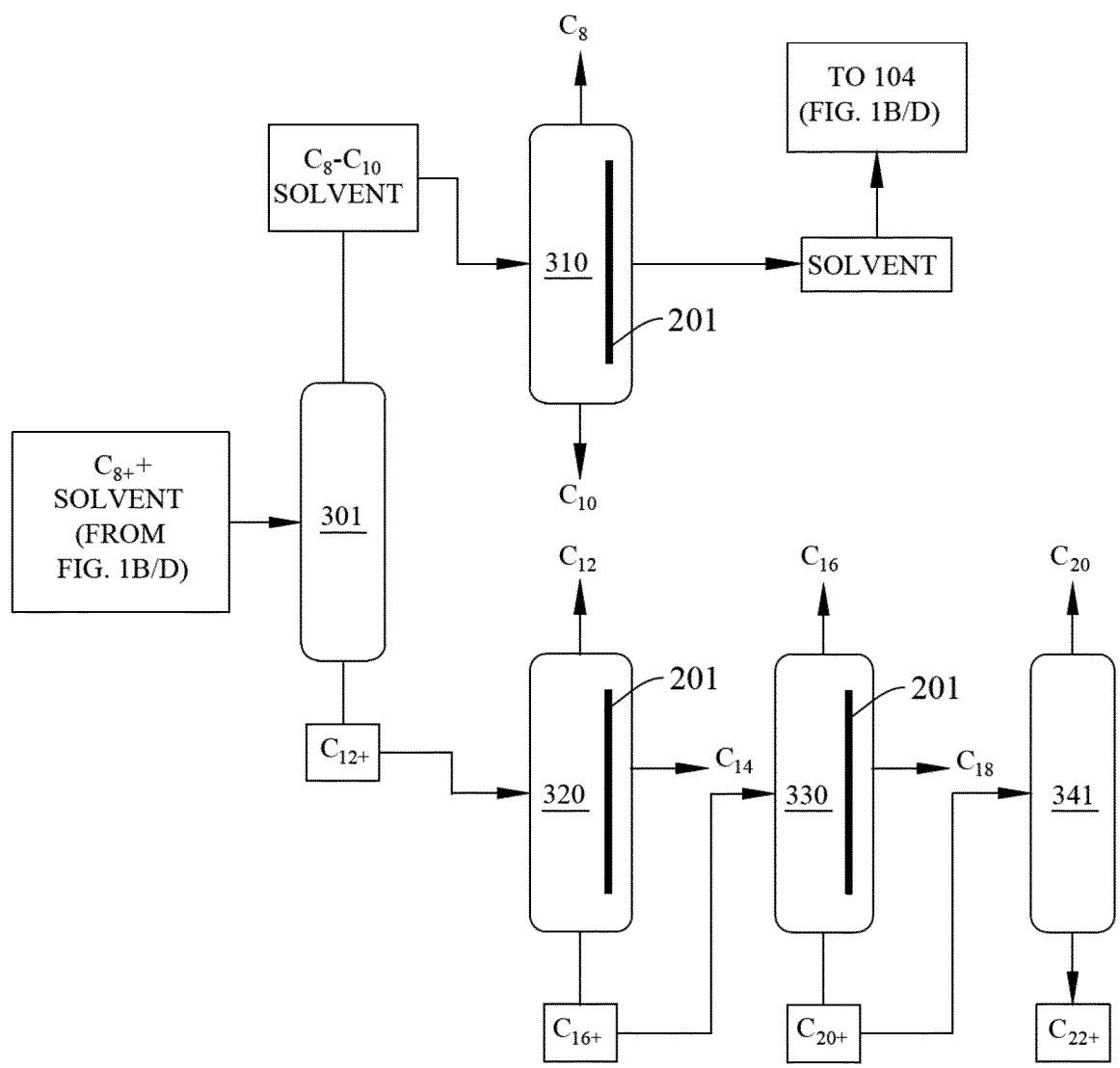
FIG. 13 shows a modified LAO separation sequence using the second distillation column configuration from FIG. 6, in which a solvent is separated downstream from $C_6$ LAOs.
Figure 14:
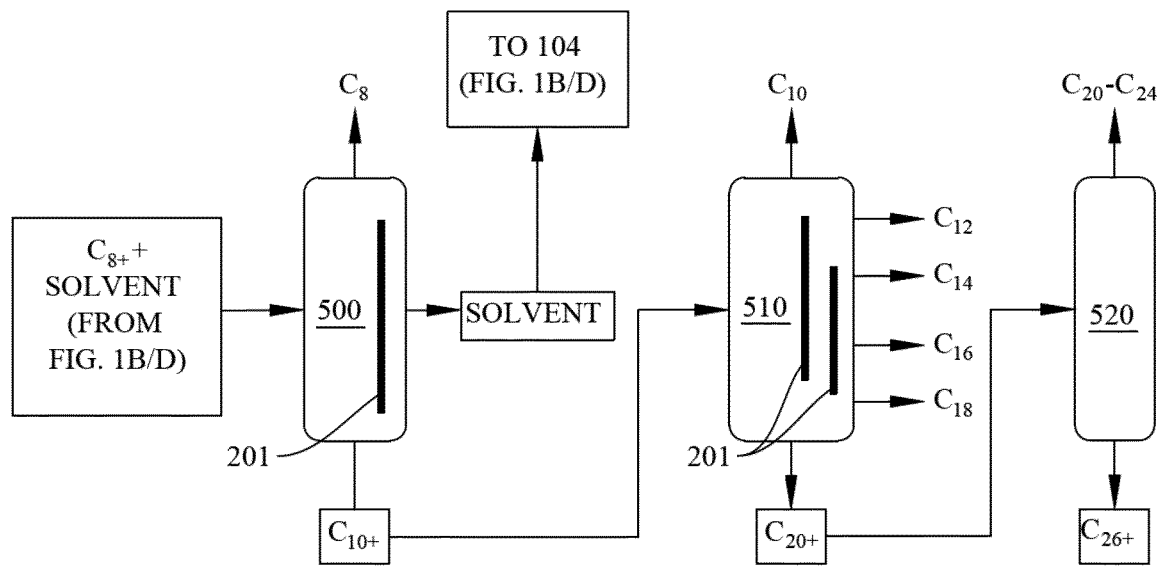
FIG. 14 shows a modified LAO separation sequence using the fourth distillation column configuration from FIG. 9, in which a solvent is separated downstream from $C_6$ LAOs.

Distillation column configurations and methods of the present disclosure employing at least one dividing wall column in a series of distillation columns will now be described in further detail by making reference to FIGS. 2A-15. Any of the series of distillation columns comprising at least one dividing wall column may further comprise at least one two-product distillation column at a terminus of the series. Use of a two-product distillation column at the terminus of the series may be beneficial when complete separation of $C_{20+}$ LAOs is not desired or energetically favorable, as discussed elsewhere herein. Alternately, a two-product distillation column may replace a terminal dividing wall column in the series in some instances. It should be further noted that although FIGS. 3A-11C show a pre-processed product stream being received from the process configuration of FIG. 1A, it is to be appreciated that the pre-processed product stream may be comparably received from the alternative process configuration of FIG. 1C. Likewise, FIGS. 12-14 show a pre-processed product stream being received from the process configuration of FIG. 1B and solvent being recycled to FIG. 1B, but it is likewise to be appreciated that the process configuration of FIG. 1D may be substituted equivalently for the receiving and recycling operations.

According to some embodiments, a pre-processed product streams comprising $C_{8+}$ LAOs may be obtained by processing a reaction product stream from a LAO synthesis reaction, such as a reaction product stream obtained from oligomerization of ethylene using a Ziegler-type catalyst. In illustrative embodiments, suitable pre-processed product streams for use in the present disclosure may be obtained by processing the reaction product stream from a LAO synthesis reactor in accordance with the procedures outlined in FIGS. 1A-1D. Namely, residual ethylene may be recycled from the reaction product stream back to the reactor used for LAO synthesis, and catalyst quenching may take place after ethylene removal takes place. $C_4$ LAOs (i.e., 1-butene) may then be removed from the reaction product stream to afford a light olefin-depleted product stream comprising $C_{6+}$ LAOs. Small amounts of residual ethylene may also be removed in conjunction with separation of $C_4$ LAOs in some cases.

Continuing with procedures for obtaining a pre-processed product stream, the light olefin-depleted product stream obtained by removal of ethylene and $C_4$ LAOs may be further processed to afford the pre-processed product stream comprising $C_{8+}$ LAOs. Namely, methods of the present disclosure may comprise providing the light olefin-depleted product stream comprising $C_{6+}$ LAOs and a solvent to a first distillation column upstream from (prior to) the series of distillation columns comprising at least one dividing wall column, and separating $C_6$ LAOs as an overhead stream from the first distillation column and $C_{8+}$ LAOs as a bottoms stream from the first distillation column, with the bottoms stream ($C_{8+}$ LAOs) being provided as the pre-processed product stream to the series of distillation columns for separating individual LAOs or mixtures of LAOs from one another. Alternately, the first distillation column may be considered to represent an initial pre-column of the series of distillation columns, with $C_6$ LAOs being the first LAO separated in the series of distillation columns.

In some embodiments, the pre-processed product stream may be depleted of solvent once the $C_{8+}$ LAOs have been obtained, as shown in the configurations of FIGS. 1A and 1C and described above. Namely, in such embodiments, methods of the present disclosure may further comprise separating solvent as a side stream from the first distillation column. Other embodiments of the present disclosure may provide a bottoms stream comprising $C_{8+}$ LAOs and solvent, as shown in the configurations of FIGS. 1B and 1D, with solvent separation taking place further downstream in the series of distillation columns. FIGS. 12-14, discussed hereinbelow, show such alternative distillation configurations in which solvent is separated from the bottoms stream in the series of distillation columns. The distillation configurations of FIGS. 3A-11C and 15, in contrast, employ a pre-processed product stream that is already depleted of solvent before providing the pre-processed product stream to the series of distillation columns.

Before discussing specific distillation configurations and methods for separating $C_{8+}$ LAOs using at least one dividing wall column within a series of distillation columns, it can be initially mentioned that an additional dividing wall column may be used in conjunction with forming a light olefin-depleted product stream suitable for subsequent processing into a pre-processed product stream. The additional dividing wall column may be upstream from (lead) the series of distillation columns used to separate $C_{8+}$ LAOs. Namely, certain methods of the present disclosure may further comprise separating residual ethylene and $C_4$ LAOs from a light olefin-containing product stream using a lead dividing wall column to provide a light olefin-depleted product stream comprising $C_{6+}$ LAOs. The residual ethylene may be the quantity of ethylene remaining in the light olefin-containing product stream following ethylene recycling and catalyst quenching. Thus, the lead dividing wall column may replace the function of lead distillation column 125 (FIGS. 1A-1D). Alternately, the lead dividing wall column may be used to facilitate recycling of all ethylene passing from the LAO synthesis reactor, in which case a separate ethylene recovery unit may be omitted. As such, capital expenditure advantages may be realized.

Figure 2A:
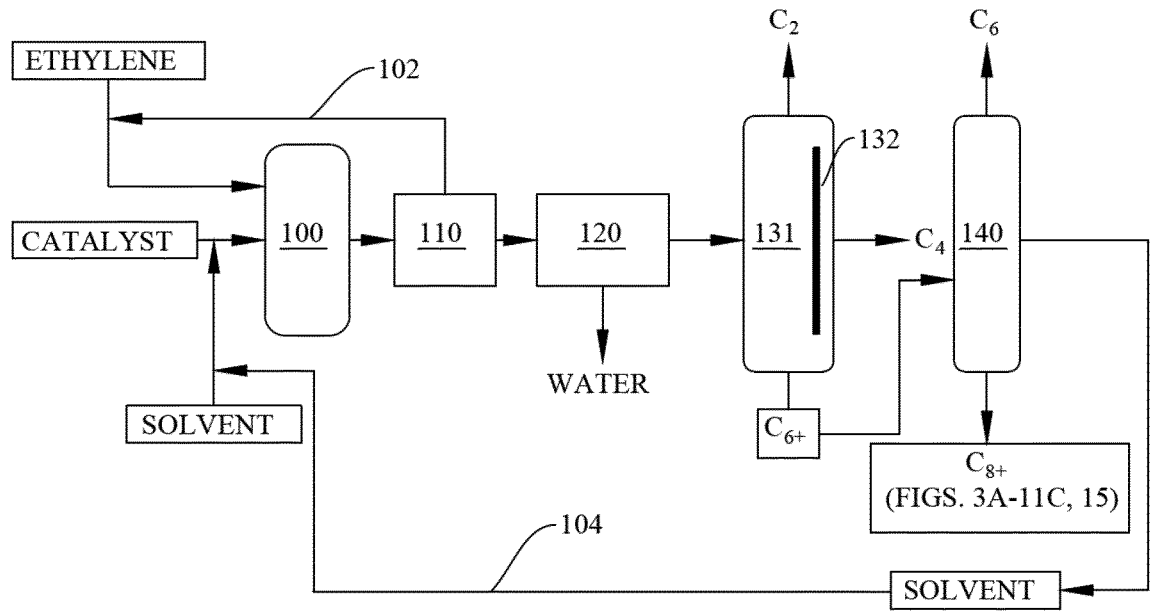
FIGS. 2A and 2B show block diagrams illustrating various operations that may be performed in the course of forming and isolating LAOs, in which a dividing wall column may be used to remove light alkenes, and which may be implemented with one or more embodiments of the present disclosure.
Figure 2B:
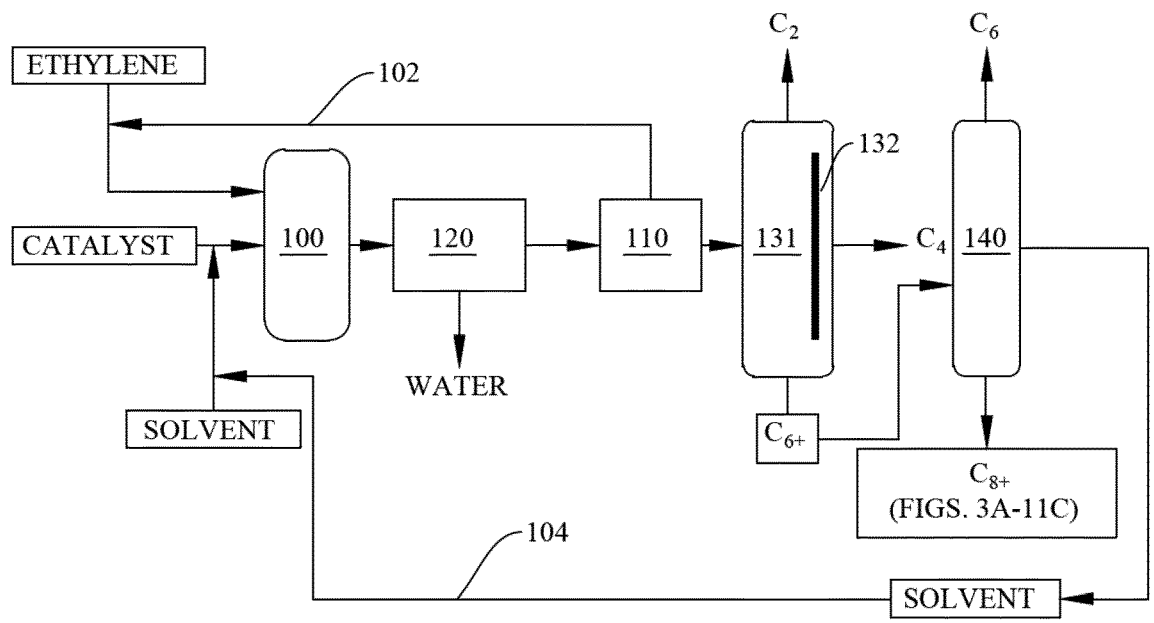

FIGS. 2A and 2B show block diagrams illustrating various operations that may be performed in the course of forming and isolating LAOs, in which a dividing wall column may be used to remove light alkenes, and which may be implemented with one or more embodiments of the present disclosure. The processing scheme illustrated in FIG. 2A is similar to that shown in FIG. 1A and common reference characters are used to denote operations or structures having substantial structural or functional similarity to one another. Namely, FIG. 2A differs from FIG. 1A in that lead distillation column 125 and light olefin distillation column 130, both two-product distillation columns in FIG. 1A, have been replaced with dividing wall column 131 containing dividing wall 132 in FIG. 2A. Instead of obtaining residual ethylene and $C_4$ LAOs as separate overhead streams, as in FIG. 1A, the $C_4$ LAOs are obtained as a side stream and residual ethylene is removed as an overhead stream from dividing wall column 131 in FIG. 2A. The processing scheme of FIG. 2A may be particularly desirable if recovery of high-purity $C_4$ LAOs is needed, which may provide capital efficiency advantages. Alternately, ethylene recovery unit 110 may be omitted if sufficient ethylene recovery may be performed with dividing wall column 131, in which case ethylene recycling line 102 may be arranged to receive the overhead stream from dividing wall column 131 (alternate configuration not depicted). Further alternately, the order to catalyst deactivation and ethylene recycling may be reversed, as depicted in FIG. 2B and corresponding to the process configuration shown in FIG. 1C. The $C_{6+}$ LAOs obtained as the bottoms stream from dividing wall column 131 may be processed in a similar manner to the corresponding bottoms stream obtained from light olefin distillation column 130 in FIG. 1A or 1C. Although not shown in the FIGS. in the interest of brevity, it is to be appreciated that dividing wall column 131 may be similarly incorporated in the processing schemes of FIGS. 1B and 1D to afford a like bottoms stream that may undergo further processing in the manner depicted therein.

Once $C_{8+}$ LAOs have been provided to the first member of the series of distillation columns, LAO separation may take place. The column configurations in the series of distillation columns disclosed herein may be such that individual LAOs having an even number of carbon atoms up to at least $C_{18}$ or $C_{20}$ are separated as individual LAOs. That is, the series of distillation columns may comprise a sufficient number of distillation columns (including at least one dividing wall column) to separate $C_8$-$C_{20}$ LAOs having an even carbon number count at different locations, either as an overhead stream or as a side stream, as individual LAOs. In some column configurations, individual LAOs up to $C_{22}$ or $C_{24}$ LAOs may be obtained. LAOs in the $C_{20+}$ range are high-boiling, waxy solids, and it may be energetically unfavorable to separate such LAOs from each other by distillation, particularly when a given LAO is present in low overall abundance. Accordingly, some embodiments of the present disclosure may leave LAOs in this carbon count range at least partially unseparated from one another. In particular embodiments of the present disclosure, mixtures of LAOs having 20 carbon atoms or more with an even number carbon count may be obtained, such as $C_{20}$-$C_{24}$ LAOs, $C_{20}$-$C_{22}$ LAOs, $C_{20}$-$C_{26}$ LAOs, $C_{24}$-$C_{26}$ LAOs, or $C_{26+}$ LAOs. Certain distillation configurations may also produce lower LAOs as mixtures, depending on application-specific requirements, such as a mixture of $C_{16}$ and $C_{18}$ LAOs, or a mixture of $C_{18}$ and $C_{20}$ LAOs. LAO mixtures of the foregoing types may be separated by alternative techniques, such as those discussed above.

Figure 3A:
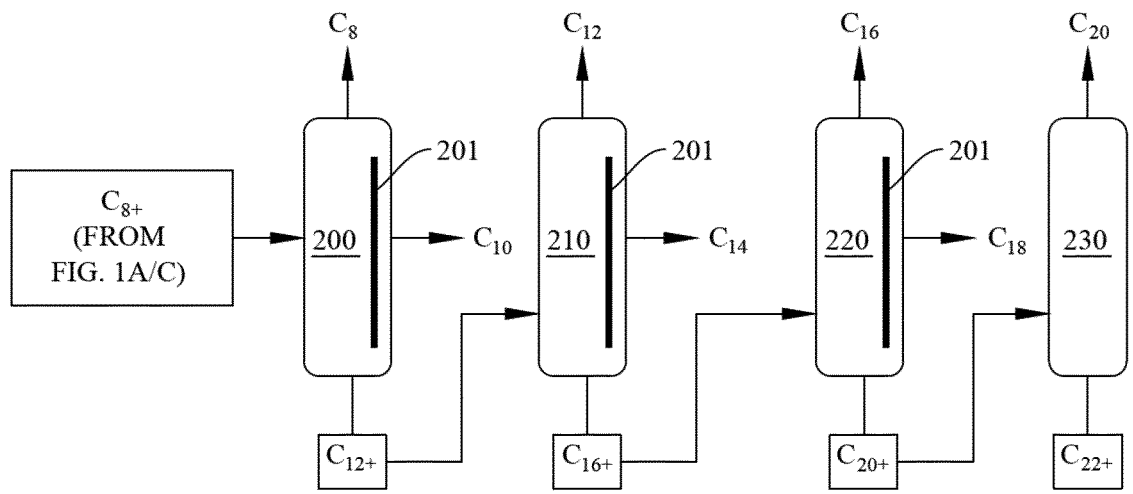
FIG. 3A shows a first distillation column configuration of the present disclosure that includes at least one dividing wall column, and which is capable of separating individual LAO fractions up to at least $C_{20}$ LAOs when provided with a pre-processed product stream comprising $C_{8+}$ LAOs. The distillation column configuration of FIG. 3A includes three dividing wall columns arranged in fluid communication sequence with one another, with a two-product distillation column arranged at a terminus of the series.
Figure 3B:
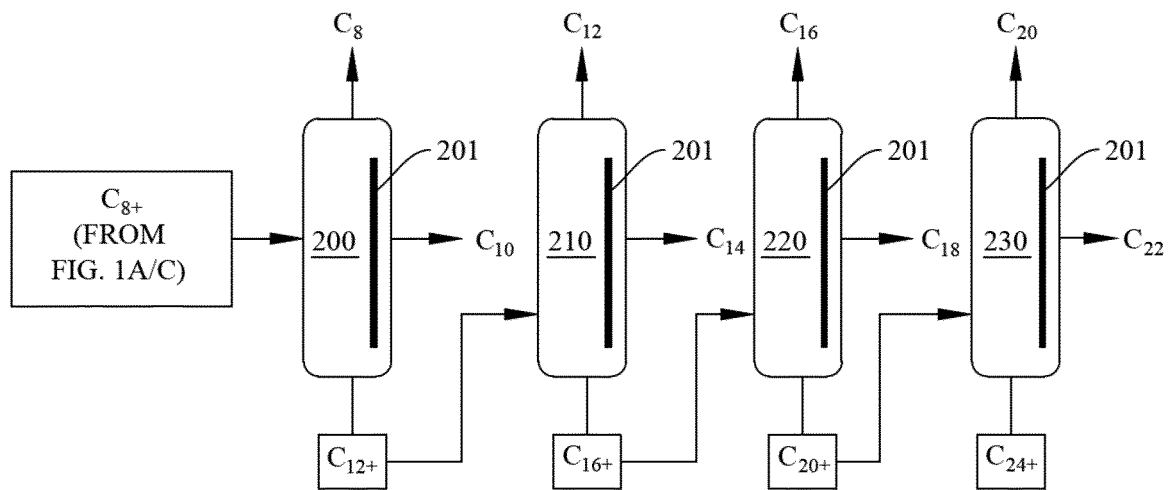
FIG. 3B shows a variant of the first distillation column configuration, in which a dividing wall column replaces the two-product distillation column at the terminus of the sequence.

In some embodiments, a first distillation column configuration of the present disclosure may include a series of distillation columns comprising three dividing wall columns linked in direct fluid communication sequence and an additional distillation column at a terminus of the series, in which the additional distillation column is a two-product distillation column or a dividing wall column. FIGS. 3A and 3B show a first distillation column configuration of the present disclosure that includes at least one dividing wall column, and which is capable of separating individual LAO fractions up to at least $C_{20}$ LAOs when provided with a pre-processed product stream comprising $C_{8+}$ LAOs. The configuration of FIG. 3A includes a terminal two-product distillation column, whereas the configuration of FIG. 3B includes a terminal dividing wall column. Illustrative LAO separation sequences are depicted in these FIGS.

Referring to FIG. 3A, dividing wall columns 200, 210 and 220 are linked to one another in direct fluid communication sequence, with dividing wall column 200 being arranged to receive a pre-processed product stream. Each of dividing wall columns 200, 210 and 220 includes dividing wall 201. A pre-processed product stream comprising $C_{8+}$ LAOs is provided to first dividing wall column 200, which separates the pre-processed product stream into $C_8$ LAOs as an overhead stream, $C_{10}$ LAOs as a side stream, and $C_{12+}$ LAOs as a bottoms stream. The bottoms stream from dividing wall column 200 is then provided to dividing wall column 210, which separates the bottoms stream into $C_{12}$ LAOs as an overhead stream, $C_{14}$ LAOs as a side stream, and $C_{16+}$ LAOs as a bottoms stream. Likewise, the bottoms stream from dividing wall column 210 is then provided to dividing wall column 220, which separates the bottoms stream into $C_{16}$ LAOs as an overhead stream, $C_{18}$ LAOs as a side stream, and $C_{20+}$ LAOs as a bottoms stream. Alternately, dividing wall column 200 may separate $C_8$ LAOs as an overhead stream, $C_{10}$ LAOs as a side stream, and $C_{12+}$ LAOs as a bottoms stream; dividing wall column 210 separates $C_{12}$ LAOs as an overhead stream, $C_{14}$ LAOs as a side stream, and $C_{16+}$ LAOs as a bottoms stream; and dividing wall column 220 separates $C_{16}$ and $C_{18}$ LAOs as an overhead stream, $C_{20}$ LAOs as a side stream, and $C_{22+}$ LAOs as a bottoms stream.

The distillation column configuration depicted in FIG. 3B shows an identical arrangement of dividing wall columns 200, 210, and 220, and a like distribution of separated LAO fractions is obtained therefrom.

Separation of at least $C_{20}$ LAOs as an individual LAO fraction occurs in additional distillation column 230 in the distillation column configurations depicted in FIGS. 3A and 3B. As depicted in FIG. 3A, additional distillation column 230 is a two-product distillation column, which provides $C_{20}$ LAOs as an overhead stream and $C_{22+}$ LAOs as a bottoms stream. In FIG. 3B, additional distillation column 230 is a dividing wall column, which provides $C_{20}$ LAOs as an overhead stream, $C_{22}$ LAOs as a side stream, and $C_{24+}$ LAOs as a bottoms stream. The $C_{22+}$ or $C_{24+}$ LAOs obtained as the bottoms stream from additional distillation column 230 may be further processed by other separation processes, such as those referenced above, to obtain even higher individual LAO fractions.

Alternative product streams may be obtained from additional distillation column 230 depending on particular application needs. For example, a two-product distillation column as additional distillation column 230 may alternately separate $C_{20}$-$C_{22}$ LAOs as an overhead stream and $C_{24+}$ LAOs as a bottoms stream; or $C_{20}$-$C_{24}$ LAOs as an overhead stream and $C_{26+}$ LAOs as a bottoms stream. Likewise a dividing wall column as additional distillation column 230 may alternately separate $C_{20}$ LAOs as an overhead stream, $C_{22}$-$C_{24}$ LAOs as a side stream, and $C_{26+}$ LAOs as a bottoms stream.

Accordingly, certain methods for separating LAOs from one another may comprise providing a pre-processed product stream comprising $C_{8+}$ LAOs to a first of three dividing wall columns, in which the first of the three dividing wall columns separates $C_8$ LAOs as an overhead stream, $C_{10}$ LAOs as a side stream, and $C_{12+}$ LAOs as a bottoms stream; a second of the three dividing wall columns separates $C_{12}$ LAOs as an overhead stream, $C_{14}$ LAOs as a side stream, and $C_{16+}$ LAOs as a bottoms stream; and a third of the three dividing wall columns separates $C_{16}$ LAOs as an overhead stream, $C_{18}$ LAOs as a side stream, and $C_{20+}$ LAOs as a bottoms stream. In further embodiments of such methods, the additional distillation column may be a two-product distillation column, with the additional distillation column separating $C_{20}$ LAOs as an overhead stream and $C_{22+}$ LAOs as a bottoms stream. In other further embodiments of such methods, the additional distillation column may be a dividing wall column, with the additional distillation column separating $C_{20}$ LAOs as an overhead stream, $C_{22}$ LAOs as a side stream, and $C_{24+}$ LAOs as a bottoms stream. Process configurations such as those depicted in FIGS. 3A and 3B may be advantageous for minimizing heating time of the LAOs, thereby limiting the potential of cracking and unwanted formation of color bodies.

Figure 4:
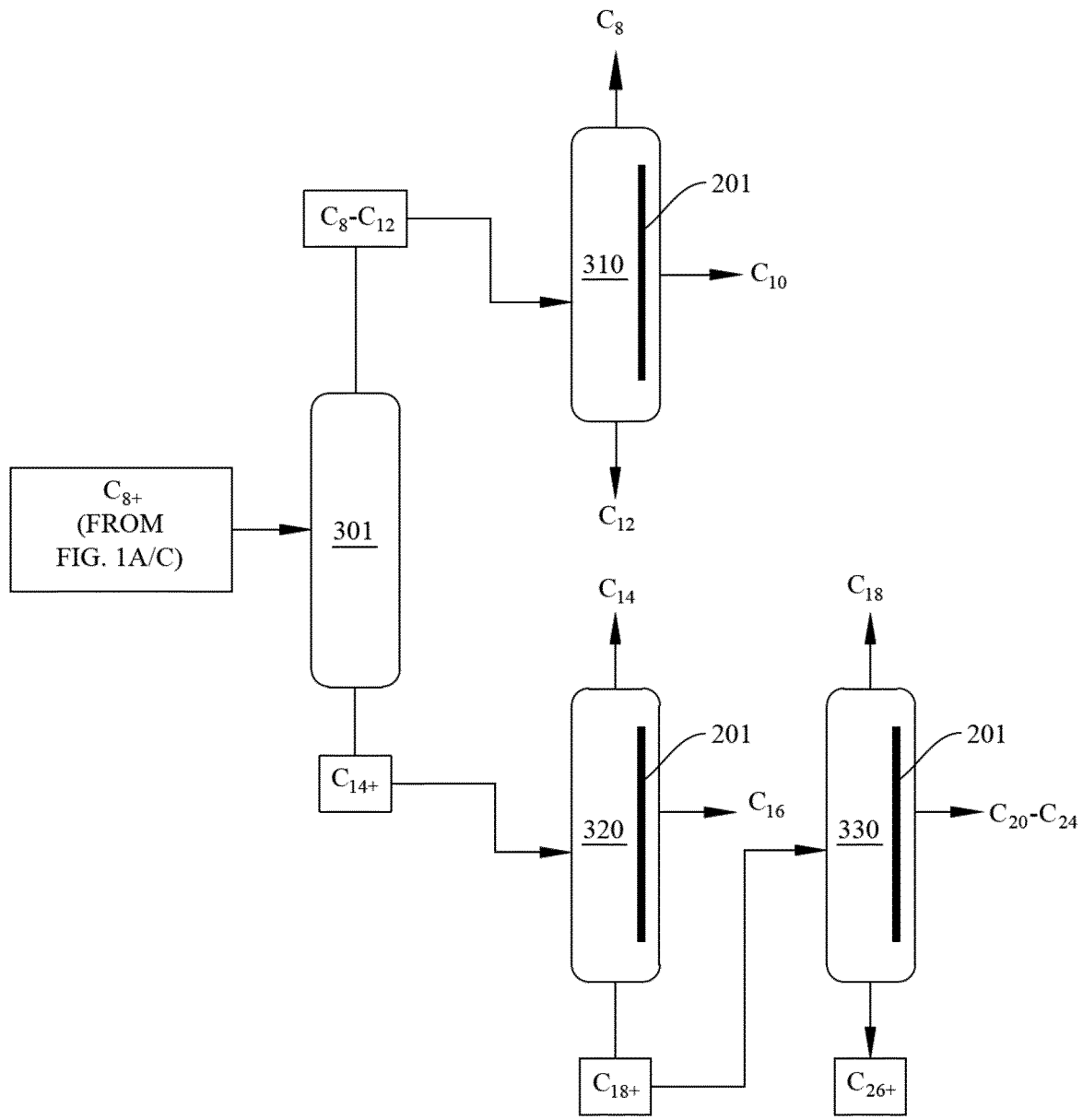
FIG. 4 shows a second distillation column configuration of the present disclosure that includes at least one dividing wall column, and which is capable of separating individual LAO fractions up to at least $C_{18}$ LAOs when provided with a pre-processed product stream comprising $C_{8+}$ LAOs. The distillation column configuration of FIG. 4 includes a two-product distillation column, a first dividing wall column arranged to receive the overhead stream from the two-product distillation column, a second dividing wall column arranged to receive the bottoms stream from the two-product distillation column, and a third dividing wall column arranged to receive the bottoms stream from the second dividing wall column.

In some embodiments, a second distillation column configuration of the present disclosure may include a series of distillation columns comprising a two-product distillation column linked in direct fluid communication sequence to a first dividing wall column and a second dividing wall column, and a third dividing wall column linked in direct fluid communication sequence to the second dividing wall column, in which the first dividing wall column is arranged to receive an overhead stream from the two-product distillation column, the second dividing wall column is arranged to receive a bottoms stream from the two-product column, and the third dividing wall column is arranged to receive a bottoms stream from the second dividing wall column. FIG. 4 shows a second distillation column configuration of the present disclosure that includes at least one dividing wall column, and which is capable of separating individual LAO fractions up to at least $C_{18}$ LAOs when provided with a pre-processed product stream comprising $C_{8+}$ LAOs. Namely, the configuration of FIG. 4 includes three dividing wall columns, in which a leading two-product distillation column is linked in direct fluid communication sequence to a first dividing wall column and a second dividing wall column, and a third dividing wall column is linked in direct fluid communication sequence to second dividing wall column.

Referring to FIG. 4, two-product distillation column 301 is arranged to receive a pre-processed product stream. Two-product distillation column 301 separates the pre-processed product stream into a lighter LAO fraction and a heavier LAO fraction, each comprising a plurality of LAOs. Namely, as depicted in FIG. 4, two-product distillation column 301 separates the pre-processed product stream into $C_8$-$C_{12}$ LAOs as an overhead stream and $C_{14+}$ LAOs as a bottoms stream. Dividing wall columns 310, 320, and 330 are positioned downstream from two-product distillation column 301. Dividing wall column 310 is arranged to receive the overhead stream from two-product distillation column 301, and dividing wall column 320 is arranged to receive the bottoms stream from two-product distillation column 301. Thus, in the configuration depicted in FIG. 4, dividing wall column 310 receives $C_8$-$C_{12}$ LAOs and separates $C_8$ LAOs as an overhead stream, $C_{10}$ LAOs as a side stream, and $C_{12}$ LAOs as a bottoms stream. Likewise, dividing wall column 320 receives the $C_{14+}$ LAOs and separates $C_{14}$ LAOs as an overhead stream, $C_{16}$ LAOs as a side stream, and $C_{18+}$ LAOs as a bottoms stream. As such, dividing wall columns 310 and 320 may operate in parallel to separate $C_8$-$C_{16}$ LAOs having an even number of carbon atoms as individual LAO fractions.

The $C_{18+}$ LAOs obtained as the bottoms stream from dividing wall column 320 pass to dividing wall column 330 for additional separation. As depicted in FIG. 4, dividing wall column 330 may separate $C_{18}$ LAOs as an overhead stream, $C_{20}$-$C_{24}$ LAOs as a side stream, and $C_{26+}$ LAOs as a bottoms stream. It is to be appreciated that the LAO fractions separated in dividing wall column 330 may differ from that depicted based upon particular application needs. Potential alternative LAO fractions that may be obtained from dividing wall column 330 include, for example, $C_{18}$ LAOs as an overhead stream, $C_{20}$-$C_{22}$ LAOs as a side stream, and $C_{24+}$ LAOs as a bottoms stream; or $C_{18}$ LAOs as an overhead stream, $C_{20}$ LAOs as a side stream, and $C_{22+}$ LAOs as a bottoms stream. Alternately, configurations omitting dividing wall column 330 may feature $C_{14}$ LAO separation as an overhead stream from dividing wall column 320, $C_{16}$-$C_{18}$ LAO separation as a side stream from dividing wall column 320, and $C_{20+}$ LAO separation as a bottoms stream from dividing wall column 320.

Figure 5:
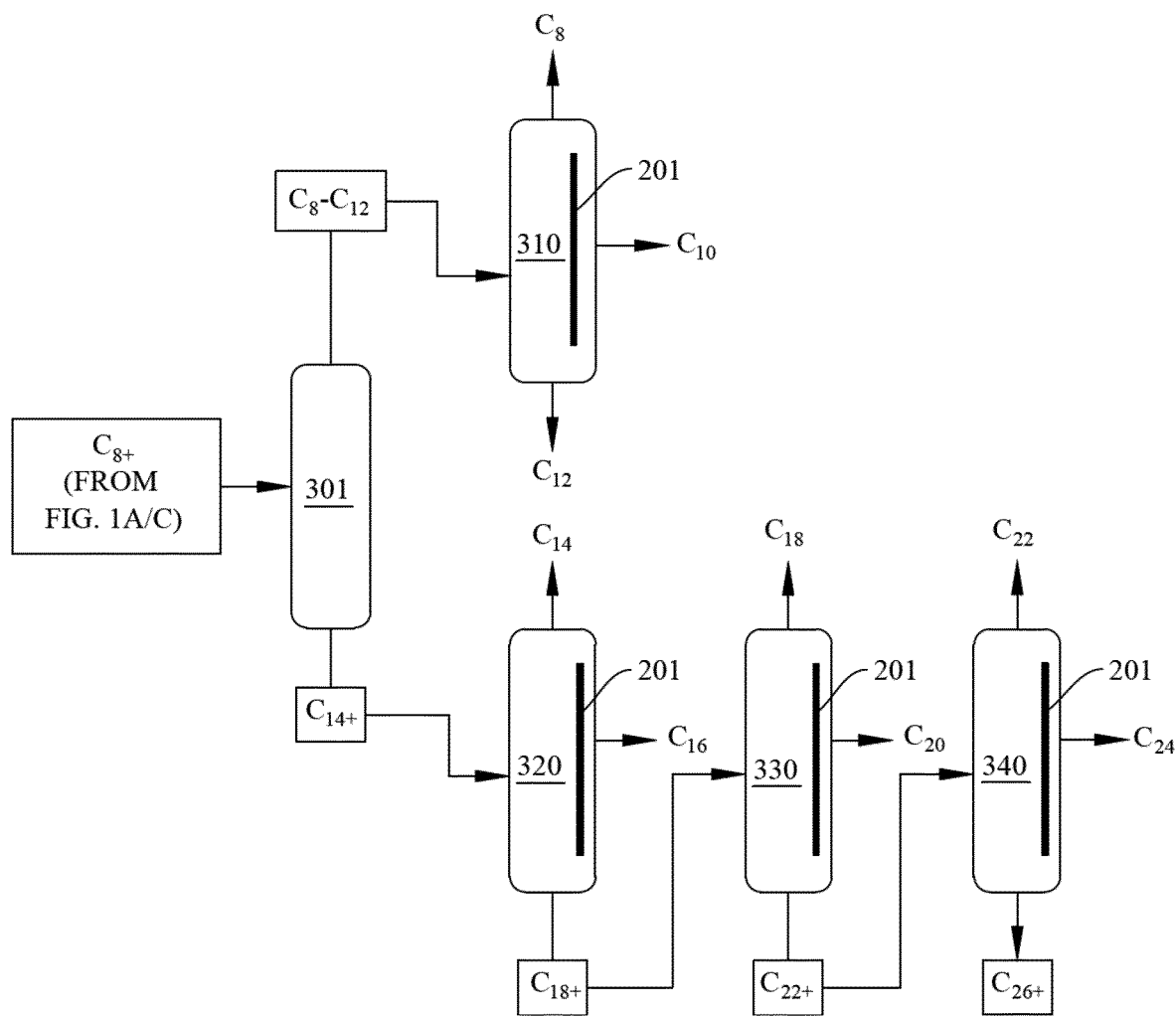
FIG. 5 shows an extension of the second distillation column configuration depicted in FIG. 4, in which a fourth dividing wall column is arranged to receive the bottoms stream from the third dividing wall column.

In further embodiments, the series of distillation columns depicted in FIG. 4 may comprise a fourth dividing wall column linked in direct fluid communication to the third dividing wall column, with the fourth dividing wall column being arranged to receive a bottoms stream from the third dividing wall column. Namely, FIG. 5 shows dividing wall column 340 arranged to receive the bottoms stream from dividing wall column 330. Dividing wall column 340 may separate additional LAO fractions from the bottoms stream of dividing wall column 330. As depicted in FIG. 5, dividing wall column 340 may separate $C_{22}$ LAOs as an overhead stream, $C_{24}$ LAOs as a side stream, and $C_{26+}$ LAOs as a bottoms stream.

Figure 6:
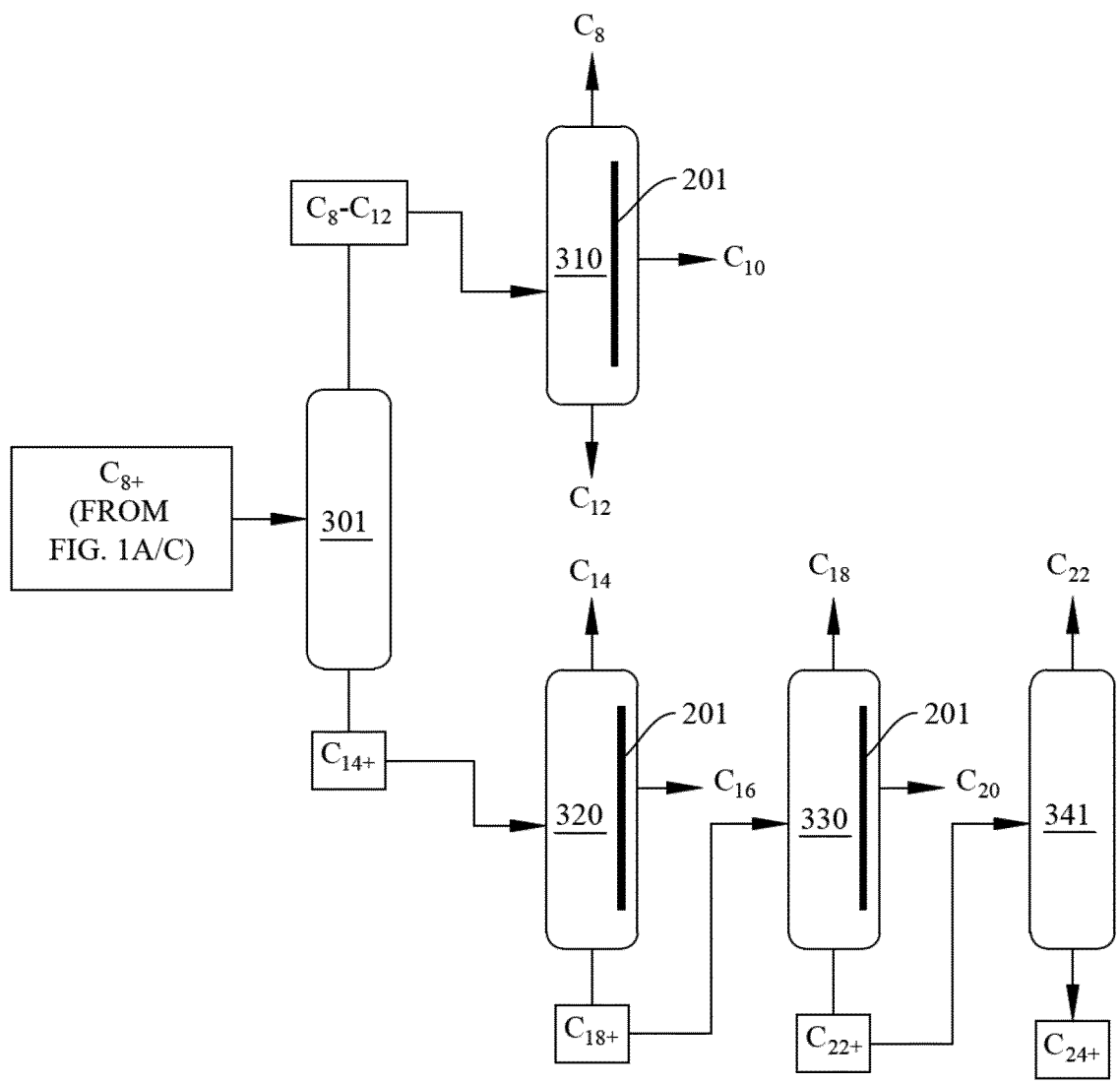
FIG. 6 shows an alternate extension of the second distillation column configuration depicted in FIG. 4, in which a second two-product distillation column is arranged to receive the bottoms stream from the third dividing wall column.

In alternate configurations to that depicted in FIG. 5, the series of distillation columns may comprise a second two-product distillation column linked in direct fluid communication sequence to the third dividing wall column, with the second two-product distillation column being arranged to receive a bottoms stream from the third dividing wall column. Namely, FIG. 6 shows two-product distillation column 341 arranged to receive the bottoms stream from dividing wall column 330. Two-product distillation column 341 may separate additional LAO fractions from the bottoms stream of dividing wall column 330. As depicted in FIG. 6, two-product distillation column 341 may separate $C_{22}$ LAOs as an overhead stream and $C_{24+}$ LAOs as a bottoms stream. Alternately, two-product distillation column 341 may separate $C_{22}$-$C_{24}$ LAOs as an overhead stream and $C_{26+}$ LAOs as a bottoms stream.

Figure 7:
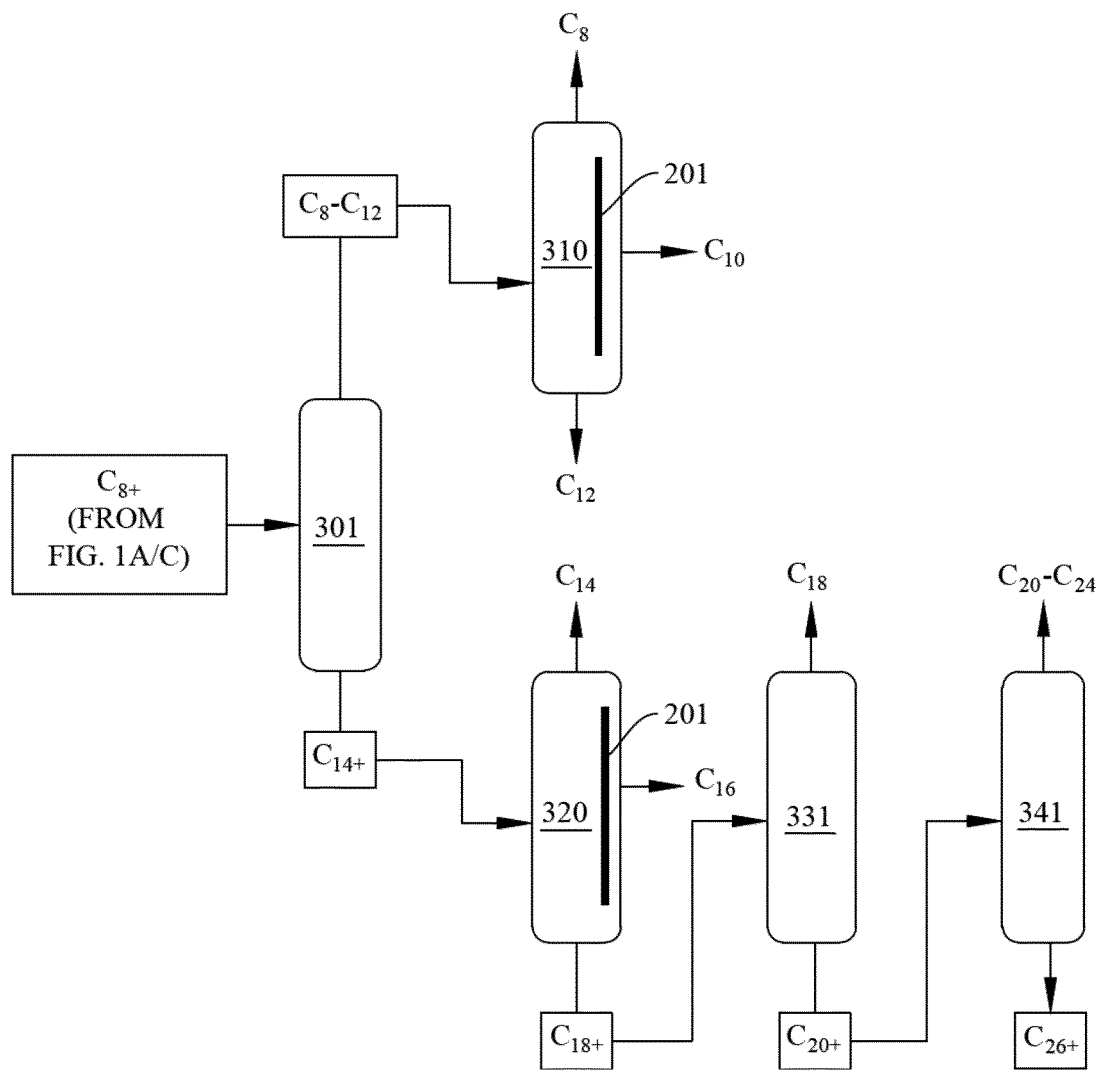
FIG. 7 shows another alternate configuration of the second distillation column configuration depicted in FIG. 4, in which a second two-product distillation column replaces the third dividing wall column and a third two-product distillation column is arranged to receive the bottoms stream from the second two-product distillation column.

In alternate configurations to that depicted in FIG. 6, a two-product distillation column may also replace the third dividing wall column. Thus, in such configurations, the series of distillation columns may comprise a first two-product distillation column linked in direct fluid communication sequence to a first dividing wall column and a second dividing wall column, a second two-product distillation column linked in direct fluid communication sequence to the second dividing wall column, and a third two-product distillation column linked in direct fluid communication sequence to the second two-product distillation column. As in similar series of distillation columns, the first dividing wall column is arranged to receive an overhead stream from the first two-product distillation column and the second dividing wall column is arranged to receive a bottoms stream from the first two-product distillation column. The second two-product distillation column is arranged to receive a bottoms stream from the second dividing wall column, and the third two-product distillation column is arranged to receive a bottoms stream from the second two-product distillation column. Namely, FIG. 7 shows two-product distillation column 341 arranged to receive the bottoms stream from two-product distillation column 331. As depicted in FIG. 7, two-product distillation column 331 may separate $C_{18}$ LAOs as an overhead stream and $C_{20+}$ LAOs as a bottoms stream. Two-product distillation column 341, in turn, may receive the bottoms stream from two-product distillation column 331 and perform additional LAO separation. As depicted in FIG. 7, two-product distillation column 341 may separate $C_{20}$-$C_{24}$ LAOs as an overhead stream and $C_{26+}$ LAOs as a bottoms stream. Alternately, two-product distillation column 341 may separate $C_{20}$-$C_{22}$ LAOs as an overhead stream and $C_{24+}$ LAOs as a bottoms stream; or $C_{20}$ LAOs as an overhead stream and $C_{22+}$ LAOs as a bottoms stream.

Figure 15:
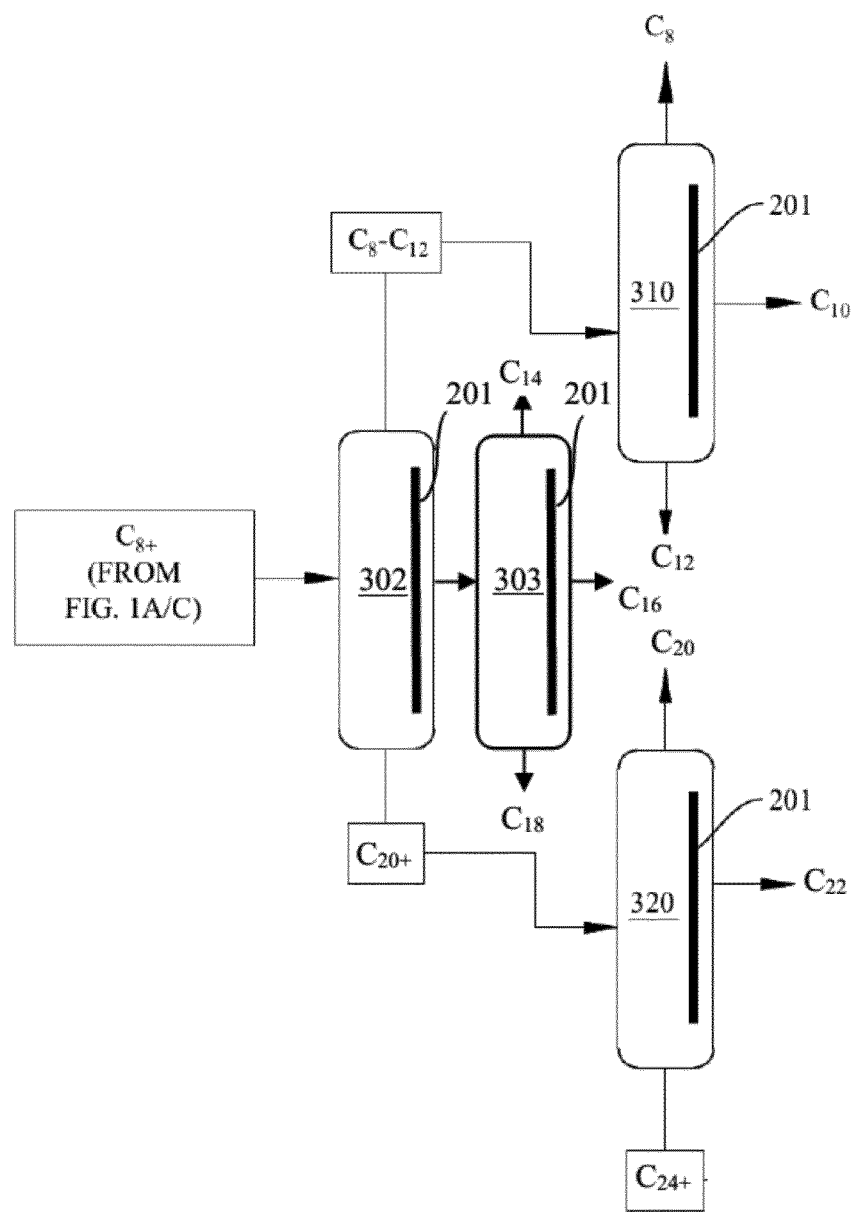
FIG. 15 shows an alternate distillation column configuration of the present disclosure that includes multiple dividing wall columns, and which is capable of separating individual LAO fractions up to at least $C_{20}$ LAOs when provided with a pre-processed product stream comprising $C_{8+}$ LAOs. The distillation column configuration of FIG. 15 includes a first dividing wall column, a second dividing wall column arranged to receive the overhead stream from the first dividing wall column, a third dividing wall column arranged to receive the side stream from the first dividing wall column, and a fourth dividing wall column arranged to receive the bottoms stream from the first dividing wall column.

Another alternate distillation column configuration is shown in FIG. 15, in which only dividing wall columns are used for fractionating a pre-processed product stream comprising $C_{8+}$ LAOs. The distillation column configuration of FIG. 15 includes a first dividing wall column, a second dividing wall column arranged to receive the overhead stream from the first dividing wall column, a third dividing wall column arranged to receive the side stream from the first dividing wall column, and a fourth dividing wall column arranged to receive the bottoms stream from the first dividing wall column. With more specific reference to FIG. 15, dividing wall column 302 receives a pre-processed product stream comprising $C_{8+}$ LAOs. Dividing wall column 302 separates $C_8$-$C_{12}$ LAOs as an overhead stream, $C_{14}$-$C_{18}$ LAOs as a side stream, and $C_{20+}$ LAOs as bottoms stream. The overhead stream from dividing wall column 302 is provided to dividing wall column 310, which then separates $C_8$ LAOs as an overhead stream, $C_{10}$ LAOs as a side stream, and $C_{12}$ LAOs as a bottoms stream. The side stream from dividing wall column 302 is provided to dividing wall column 303, which separates $C_{14}$ LAOs as an overhead stream, $C_{16}$ LAOs as a side stream, and $C_{18}$ LAOs as a bottoms stream. The $C_{20+}$ LAOs in the bottoms stream from dividing wall column 302 are provided to dividing wall column 320 for additional separation. As depicted in FIG. 15, dividing wall column 320 separates $C_{20}$ LAOs as an overhead stream, $C_{22}$ LAOs as a side stream, and $C_{24+}$ LAOs as a bottoms stream. Alternately, dividing wall column 320 may separate $C_{20}$ LAOs as an overhead stream, $C_{22}$-$C_{24}$ LAOs as a side stream, and $C_{26+}$ LAOs as a bottoms stream, or $C_{20}$-$C_{22}$ LAOs as an overhead stream, $C_{24}$ LAOs as a side stream, and $C_{26+}$ LAOs as a bottoms stream, or $C_{20}$-$C_{22}$ LAOs as an overhead stream, $C_{24}$-$C_{26}$ LAOs as a side stream, and $C_{28+}$ LAOs as a bottoms stream, or $C_{20}$-$C_{24}$ LAOs as an overhead stream, $C_{26}$ LAOs as a side stream, and $C_{28+}$ LAOs as a bottoms stream. Still further alternately, a two-product distillation column may replace dividing wall column 320.

Accordingly, certain methods for separating LAOs from one another may comprise providing a pre-processed product stream comprising $C_{8+}$ LAOs to a first two-product distillation column, with the first two-product distillation column separating $C_8$-$C_{12}$ LAOs as an overhead stream and $C_{14+}$ LAOs as a bottoms stream; a first dividing wall column separating $C_8$ LAOs as an overhead stream, $C_{10}$ LAOs as a side stream, and $C_{12}$ LAOs as a bottoms stream; and a second dividing wall column separating $C_{14}$ LAOs as an overhead stream, $C_{16}$ LAOs as a side stream, and $C_{18+}$ LAOs as a bottoms stream. According to further embodiments of the methods, a third dividing wall column may separate $C_{18}$ LAOs as an overhead stream, $C_{20}$-$C_{24}$ LAOs as a side stream, and $C_{24+}$ LAOs as a bottoms stream; $C_{18}$ LAOs as an overhead stream, $C_{20}$-$C_{22}$ LAOs as a side stream, and $C_{24+}$ LAOs as a bottoms stream; or $C_{18}$ LAOs as an overhead stream, $C_{20}$ LAOs as a side stream, and $C_{22+}$ LAOs as a bottoms stream. According to still further embodiments of the methods, the third dividing wall column may separate $C_{18}$ LAOs as an overhead stream, $C_{20}$ LAOs as a side stream, and $C_{22+}$ LAOs as a bottoms stream; and a fourth dividing wall column in direct fluid communication sequence with the third dividing wall column may separate $C_{22}$ LAOs as an overhead stream, $C_{24}$ LAOs as a side stream, and $C_{26+}$ LAOs as a bottoms stream. According to still other further embodiments of the methods, the third dividing wall column may separate $C_{18}$ LAOs as an overhead stream, $C_{20}$ LAOs as a side stream, and $C_{22+}$ LAOs as a bottoms stream; and a second two-product distillation column in direct fluid communication sequence with the third dividing wall column may separate $C_{22}$ LAOs as an overhead stream and $C_{24+}$ LAOs as a bottoms stream; or $C_{22}$-$C_{24}$ LAOs as an overhead stream and $C_{26+}$ LAOs as a bottoms stream.

Other embodiments of methods for separating LAOs from one another according to the present disclosure may comprise providing a pre-processed product stream comprising $C_{8+}$ LAOs to a first two-product distillation column, with the first two-product distillation column separating $C_8$-$C_{12}$ LAOs as an overhead stream and $C_{14+}$ LAOs as a bottoms stream; a first dividing wall column separating $C_8$ LAOs as an overhead stream, $C_{10}$ LAOs as a side stream, and $C_{12}$ LAOs as a bottoms stream; a second dividing wall column separating $C_{14}$ LAOs as an overhead stream, $C_{16}$ LAOs as a side stream, and $C_{18+}$ LAOs as a bottoms stream; a second two-product distillation column separating $C_{18}$ LAOs as an overhead stream and $C_{20+}$ LAOs as a bottoms stream; and a third two-product distillation column separating $C_{20}$-$C_{24}$ LAOs as an overhead stream and $C_{26+}$ LAOs as a bottoms stream; $C_{20}$-$C_{22}$ LAOs as an overhead stream and $C_{24+}$ LAOs as a bottoms stream; or $C_{20}$ LAOs as an overhead stream and $C_{22+}$ LAOs as a bottoms stream.

In some embodiments, the series of distillation columns employed in the disclosure herein may include at least one dividing wall column, with one or more of the at least one dividing wall column being a dual dividing wall column. The dual dividing wall column(s) may be present at any location within the series of distillation columns. Moreover, the dual dividing wall column(s) may be configured to separate a desired number of LAO fractions as individual LAO side streams. In illustrative embodiments, the dual dividing wall column(s) may be configured to separate two side streams, three side streams, or four side streams, each side stream featuring substantially an individual LAO. Each dual dividing wall column may likewise provide an overhead stream and a bottoms stream, with the bottoms stream being provided to a subsequent distillation column in some instances. Particular configurations including at least one dual dividing wall column within the series of distillation columns are provided hereinafter.

In some embodiments, a third distillation column configuration of the present disclosure may include a series of distillation columns comprising a dual dividing wall column as a first member of the series of distillation columns and a second member of the series of distillation columns may comprise a dividing wall column, with the dual dividing wall column and the dividing wall column being linked in direct fluid communication sequence. In an extension of the series of distillation columns, a second dividing wall column or a two-product distillation column may be in direct fluid communication sequence with the other dividing wall column and be arranged to receive a bottoms stream therefrom. FIGS. 8A-8D show the third distillation column configuration of the present disclosure, in which a dual dividing wall column is present as a first member of a series of distillation columns and a dividing wall column is present as a second member of the series of distillation columns, optionally with another dividing wall column present as a third member of the series (FIGS. 8B-8D). Optionally, a two-product distillation column may constitute the third member of the series (column configuration not shown in the FIGS.).

Figure 8A:
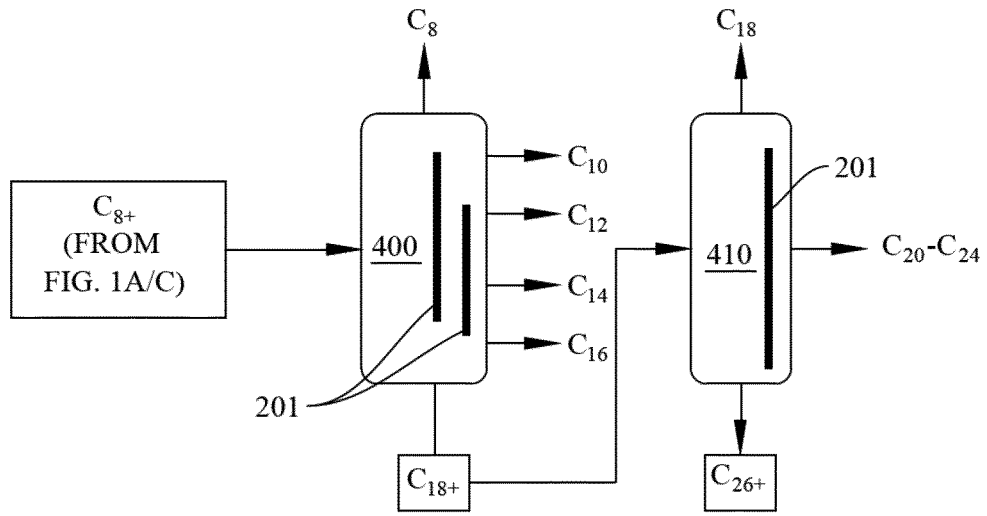
FIGS. 8A-8D show a third distillation column configuration of the present disclosure that includes at least one dividing wall column, one or more of which is a dual dividing wall column, and which is capable of separating individual LAO fractions up to at least $C_{20}$ LAOs when provided with a pre-processed product stream comprising $C_{8+}$ LAOs. The distillation column configuration of FIG. 8A includes a series of distillation columns having a dual dividing wall column as a first member of the series and a dividing wall column as a second member of the series, in which the dual dividing wall column is configured to separate four side streams therefrom. The distillation column configuration of FIG. 8B extends the series of distillation columns with an additional dividing wall distillation column in direct fluid communication sequence with the dividing wall column. The distillation column configuration of FIG. 8C is a variant of the distillation column configuration of FIG. 8B, in which the dual dividing wall column is configured to separate three side streams therefrom. The distillation column configuration of FIG. 8D is a variant of the distillation column configuration of FIG. 8B, in which the dual dividing wall column is configured to separate two side streams therefrom.
Figure 8B:
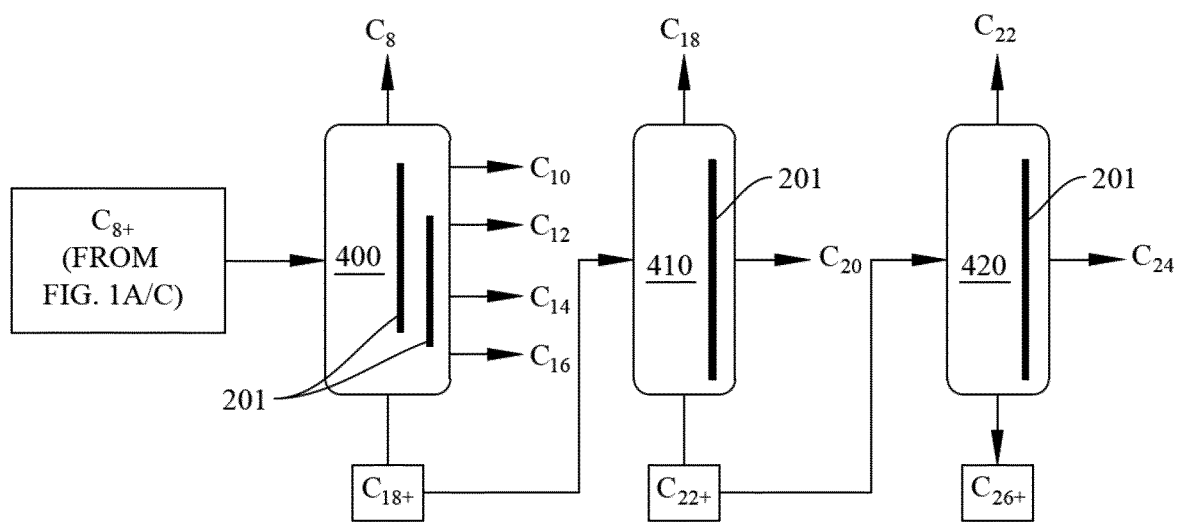
Figure 8C:
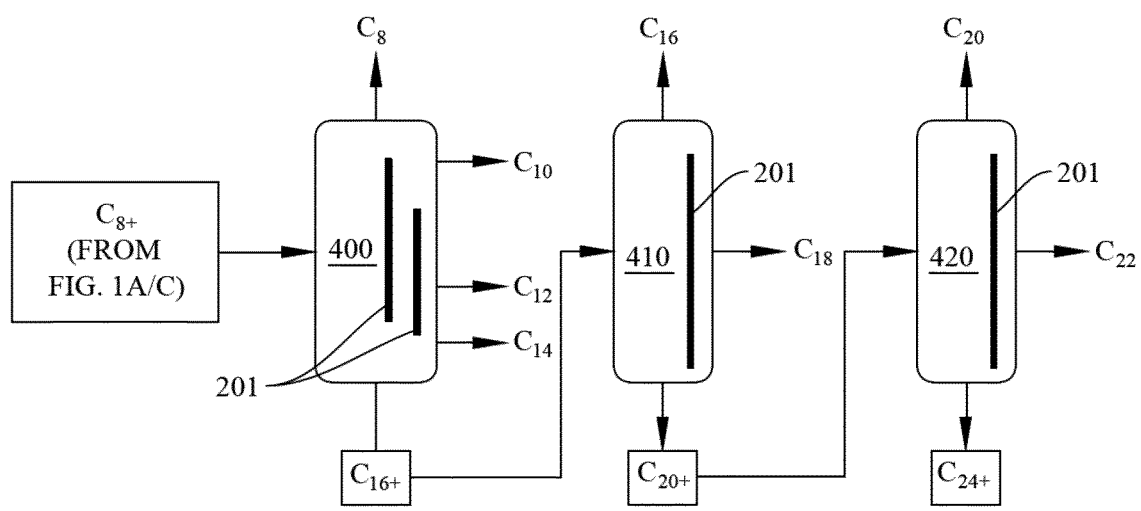
Figure 8D:
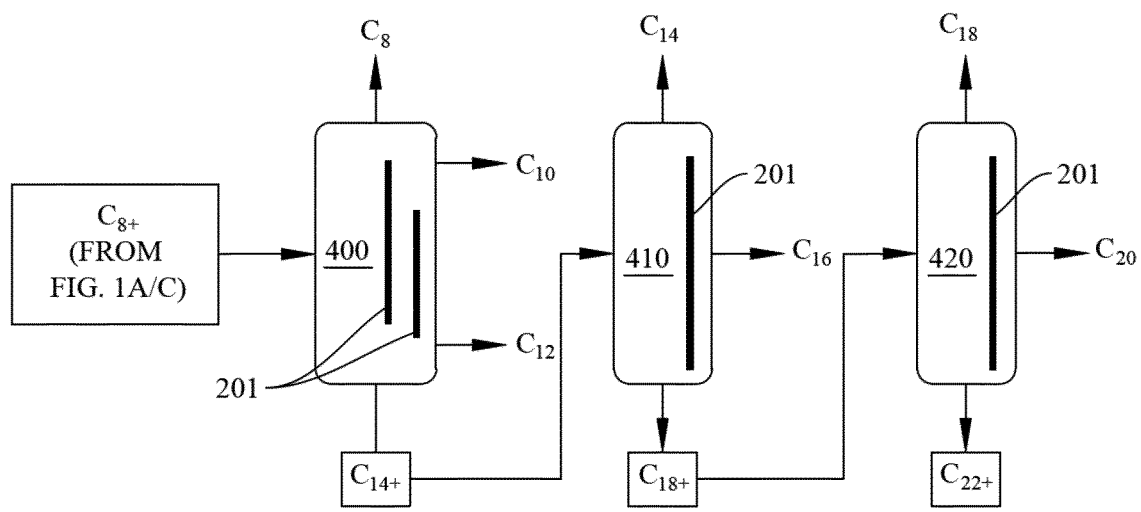

Referring to FIG. 8A, dual dividing wall column 400 is arranged to receive a pre-processed product stream comprising $C_{8+}$ LAOs. In the depicted configuration, dual dividing wall column 400 is adapted to separate four side streams therefrom, each comprising a different individual LAO. Namely, as depicted, dual dividing wall column 400 separates $C_8$ LAOs as an overhead stream, $C_{10}$ LAOs as a first side stream, $C_{12}$ LAOs as a second side stream, $C_{14}$ LAOs as a third side stream, $C_{16}$ LAOs as a fourth side stream, and $C_{18+}$ LAOs as a bottoms stream. Dividing wall column 410 receives the bottoms stream from dual dividing wall column 400 and separates $C_{18}$ LAOs as an overhead stream, $C_{20}$-$C_{24}$ LAOs as a side stream, and $C_{26+}$ LAOs as a bottoms stream; $C_{18}$ LAOs as an overhead stream, $C_{20}$-$C_{22}$ LAOs as a side stream, and $C_{24+}$ LAOs as a bottoms stream; or $C_{18}$ LAOs as an overhead stream, $C_{20}$ LAOs as a side stream, and $C_{22+}$ LAOs as a bottoms stream.

FIG. 8B shows an extension of the series of distillation columns depicted in FIG. 8A, in which additional dividing wall column 420 is present and arranged to receive the bottoms stream from dividing wall column 410. Namely, as depicted in FIG. 8B, dividing wall column 410 may provide $C_{18}$ LAOs as an overhead stream, $C_{20}$ LAOs as a side stream, and $C_{22+}$ LAOs as a bottoms stream, and additional dividing wall column 420 may provide $C_{22}$ LAOs as an overhead stream, $C_{24}$ LAOs as a side stream, and $C_{26+}$ LAOs as a bottoms stream. Dual dividing wall column 400 separates $C_8$-$C_{14}$ LAOs as in FIG. 8A. As referenced above, a variant (not shown) of the series of distillation columns shown in FIG. 8B may include a two-product distillation column in place of additional dividing wall column 420, with the LAO product distribution obtained therefrom potentially differing from that depicted.

Likewise, the number of side streams separated by dual dividing wall column 400 may differ from that depicted in FIGS. 8A and 8B. FIG. 8C shows a variant of the distillation column configuration of FIG. 8B, in which dual dividing wall column 400 is configured to separate three side streams therefrom. Namely, as depicted in FIG. 8C, dual dividing wall column 400 may provide $C_8$ LAOs as an overhead stream, $C_{10}$ LAOs as a first side stream, $C_{12}$ LAOs as a second side stream, $C_{14}$ LAOs as a third side stream, and $C_{16+}$ LAOs as a bottoms stream. Dividing wall column 410 may separate $C_{16}$ LAOs as an overhead stream, $C_{18}$ LAOs as a side stream, and $C_{20+}$ LAOs as a bottoms stream, and additional dividing wall column 420 may provide $C_{20}$ LAOs as an overhead stream, $C_{22}$ LAOs as a side stream, and $C_{24+}$ LAOs as a bottoms stream; or $C_{20}$ LAOs as an overhead stream, $C_{22}$-$C_{24}$ LAOs as a side stream, and $C_{26+}$ LAOs as a bottoms stream. As referenced above, a variant (not shown) of the series of distillation columns shown in FIG. 8C may include a two-product distillation column in place of additional dividing wall column 420, with the LAO product distribution obtained therefrom potentially differing from that depicted. Another variant (not shown) of the series of distillation columns shown in FIG. 8C may omit additional dividing wall column 420 or a corresponding conventional dividing wall column.

FIG. 8D shows another variant of the distillation column configuration of FIG. 8B, in which dual dividing wall column 400 is configured to separate two side streams therefrom. Namely, as depicted in FIG. 8D, dual dividing wall column 400 may provide $C_8$ LAOs as an overhead stream, $C_{10}$ LAOs as a first side stream, $C_{12}$ LAOs as a second side stream, and $C_{14+}$ LAOs as a bottoms stream. Dividing wall column 410 may separate $C_{14}$ LAOs as an overhead stream, $C_{16}$ LAOs as a side stream, and $C_{18+}$ LAOs as a bottoms stream, and additional dividing wall column 420 may provide $C_{18}$ LAOs as an overhead stream, $C_{20}$ LAOs as a side stream, and $C_{22+}$ LAOs as a bottoms stream. As referenced above, a variant (not shown) of the series of distillation columns shown in FIG. 8D may include a two-product distillation column in place of dividing wall column 420. Another variant (not shown) of the series of distillation columns shown in FIG. 8D may omit additional dividing wall column 420 or a corresponding conventional dividing wall column.

Accordingly, certain methods for separating LAOs from one another may comprise providing a pre-processed product stream comprising $C_{8+}$ LAOs to a series of distillation columns comprising a dual dividing wall column and a dividing wall column linked in fluid communication sequence, in which the dual dividing wall column separates $C_8$ LAOs as an overhead stream, $C_{10}$ LAOs as a first side stream, $C_{12}$ LAOs as a second side stream, $C_{14}$ LAOs as a third side stream, $C_{16}$ LAOs as a fourth side stream, and $C_{18+}$ LAOs as a bottoms stream, and the dividing wall column separates $C_{18}$ LAOs as an overhead stream, $C_{20}$ LAOs as a side stream, and $C_{22+}$ LAOs as a bottoms stream; $C_{18}$ LAOs as an overhead stream, $C_{20}$-$C_{22}$ LAOs as a side stream, and $C_{24+}$ LAOs as a bottoms stream; or $C_{18}$ LAOs as an overhead stream, $C_{20}$-$C_{24}$ LAOs as a side stream, and $C_{26+}$ LAOs as a bottoms stream. Again, improved capital efficiency and a decreased propensity toward cracking and color body formation may be realized in such process configurations.

Figure 9:
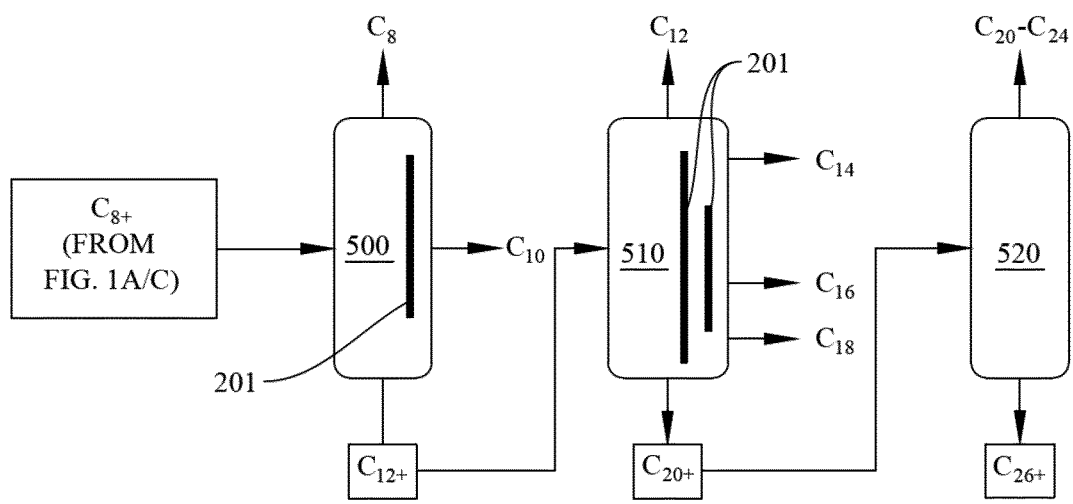
FIGS. 9 and 10 show illustrative embodiments of a fourth distillation column configuration of the present disclosure that includes at least one dividing wall column, one or more of which is a dual dividing wall column, and which is capable of separating individual LAO fractions up to at least $C_{20}$ LAOs when provided with a pre-processed product stream comprising $C_{8+}$ LAOs. The distillation column configurations of FIGS. 9 and 10 include a series of distillation columns having a dividing wall column as a first member of the series, a dual dividing wall column as a second member of the series, and a two-product distillation column as a third member of the series.

In some embodiments, a fourth distillation column configuration of the present disclosure may include a series of distillation columns comprising a dividing wall column as a first member of the series of distillation columns and dual dividing wall column as a second member of the series of distillation columns, with the dividing wall column and the dual dividing wall column being linked in direct fluid communication sequence. In an extension of the series of distillation columns, a second dividing wall column or a two-product distillation column may be in direct fluid communication sequence with the dual dividing wall column and arranged to receive a bottoms stream therefrom. FIGS. 9 and 10 show illustrative embodiments of the fourth distillation column configuration of the present disclosure, in which a dividing wall column is present as a first member of a series of distillation columns, a dual dividing wall column is present as a second member of the series of distillation columns, and a two-product distillation column is present as a third member of the series of distillation columns. Optionally, a second dividing wall column may replace the two-product distillation column in the foregoing configurations.

Referring to FIG. 9, dividing wall column 500 is arranged to receive a pre-processed product stream comprising $C_{8+}$ LAOs. In the depicted configuration, dividing wall column 500 separates $C_8$ LAOs as an overhead stream, $C_{10}$ LAOs as a side stream, and $C_{12+}$ LAOs as a bottoms stream. Dual dividing wall column 510 receives the bottoms stream from dividing wall column 500 and separates $C_{12}$ LAOs as an overhead stream, $C_{14}$ LAOs as a first side stream, $C_{16}$ LAOs as a second side stream, $C_{18}$ LAOs as a third side stream, and $C_{20+}$ LAOs as a bottoms stream. Distillation column 520, which is a two-product distillation column linked in direct fluid communication sequence to dual dividing wall column 510 in the configuration depicted in FIG. 9, receives the bottoms stream from dual dividing wall column 510 and separates $C_{20}$-$C_{24}$ LAOs as an overhead stream and $C_{26+}$ LAOs as a bottoms stream. Alternately distillation column 520 may separate $C_{20}$ LAOs as an overhead stream and $C_{22+}$ LAOs as a bottoms stream; or $C_{20}$-$C_{22}$ LAOs as an overhead stream and $C_{24+}$ LAOs as a bottoms stream. As referenced above, a variant (not shown) of the series of distillation columns shown in FIG. 9 may include a dividing wall column in place of distillation column 520, with the LAO product distribution obtained therefrom potentially differing from that depicted. As still another variant (not shown) of the configuration shown in FIG. 9, distillation column 520 may be omitted in some embodiments.

The configuration depicted in FIG. 10 differs from that depicted in FIG. 9, in that dual dividing wall column 510 is configured to remove four side streams, with the distribution of LAO products being adjusted accordingly. In the configuration depicted in FIG. 10, the bottoms stream comprising $C_{12+}$ LAOs is again received by dual dividing wall column 510, but in this case, dual dividing wall column 510 separates $C_{12}$ LAOs as an overhead stream, $C_{14}$ LAOs as a first side stream, $C_{16}$ LAOs as a second side stream, $C_{18}$ LAOs as a third side stream, $C_{20}$ LAOs as a fourth side stream, and $C_{22+}$ LAOs as a bottoms stream. The bottoms stream comprising $C_{22+}$ LAOs is received by distillation column 520, which may separate $C_{22}$-$C_{24}$ LAOs as an overhead stream and $C_{26+}$ LAOs as a bottoms stream; or $C_{22}$ LAOs as an overhead stream and $C_{24+}$ LAOs as a bottoms stream. As referenced above, a variant (not shown) of the series of distillation columns shown in FIG. 10 may include a dividing wall column in place of distillation column 520, with the LAO product distribution obtained therefrom potentially differing from that depicted. As still another variant (not shown) of the configuration shown in FIG. 10, distillation column 520 may be omitted in some embodiments.

Accordingly, certain methods for separating LAOs from one another may comprise providing a pre-processed product stream comprising $C_{8+}$ LAOs to a series of distillation columns comprising a dividing wall column and a dual dividing wall column linked in fluid communication sequence, in which the dividing wall column separates $C_8$ LAOs as an overhead stream, $C_{10}$ LAOs as a side stream, and $C_{12+}$ LAOs as a bottoms stream, and the dual dividing wall column may separate $C_{12}$ LAOs as an overhead stream, $C_{14}$ LAOs as a first side stream, $C_{16}$ LAOs as a second side stream, $C_{18}$ LAOs as a third side stream, and $C_{20+}$ LAOs as a bottoms stream. In such embodiments, the series of distillation columns further comprises a two-product distillation column linked in direct fluid communication sequence to the dual dividing wall column, with the two-product distillation column separating $C_{20}$ LAOs as an overhead stream and $C_{22+}$ LAOs as a bottoms stream; $C_{20}$-$C_{22}$ LAOs as an overhead stream and $C_{24+}$ LAOs as a bottoms stream; or $C_{20}$-$C_{24}$ LAOs as an overhead stream and $C_{26+}$ LAOs as a bottoms stream. Alternately, the dual dividing wall column may separate $C_{12}$ LAOs as an overhead stream, $C_{14}$ LAOs as a first side stream, $C_{16}$ LAOs as a second side stream, $C_{18}$ LAOs as a third side stream, $C_{20}$ LAOs as a fourth side stream, and $C_{22+}$ LAOs as a bottoms stream. In such embodiments, the series of distillation columns may further comprise a two-product distillation column linked in direct fluid communication sequence to the dual dividing wall column, with the two-product distillation column separating $C_{22}$ LAOs as an overhead stream and $C_{24+}$ LAOs as a bottoms stream; or $C_{22}$-$C_{24}$ LAOs as an overhead stream and $C_{26+}$ LAOs as a bottoms stream.

In some embodiments, a fifth distillation column configuration of the present disclosure may include a series of distillation columns comprising a first dual dividing wall column as a first member of the series of distillation columns and second dual dividing wall column as a second member of the series of distillation columns, with the first dual dividing wall column and the second dual dividing wall column being linked in direct fluid communication sequence. FIGS. 11A-11C show illustrative embodiments of the fifth distillation column configuration of the present disclosure, in which a first dual dividing wall column is present as a first member of a series of distillation columns, a second dual dividing wall column is present as a second member of the series of distillation columns, and a two-product distillation column is present as a third member of the series of distillation columns. Optionally, the two-product distillation column may be omitted in the foregoing configurations.

Referring to FIG. 11A, dual dividing wall column 600 is arranged to receive a pre-processed product stream comprising $C_{8+}$ LAOs. In the depicted configuration, dual dividing wall column 600 separates $C_8$ LAOs as an overhead stream, $C_{10}$ LAOs as a first side stream, $C_{12}$ LAOs as a second side stream, $C_{14}$ LAOs as a third side stream, $C_{16}$ LAOs as a fourth side stream, and $C_{18+}$ LAOs as a bottoms stream. Dual dividing wall column 610 receives the bottoms stream from dual dividing wall column 600 and separates $C_{18}$ LAOs as an overhead stream, $C_{20}$ LAOs as a first side stream, $C_{22}$ LAOs as a second side stream, and $C_{24+}$ LAOs as a bottoms stream. Distillation column 620, which is a two-product distillation column linked in direct fluid communication sequence to dual dividing wall column 610 in the configuration depicted in FIG. 11A, receives the bottoms stream from dual dividing wall column 610 and separates $C_{24}$ LAOs as an overhead stream and $C_{26+}$ LAOs as a bottoms stream. In another variant (not shown) of the configuration shown in FIG. 11A, distillation column 620 may be omitted in some embodiments.

The configuration depicted in FIG. 11B differs from that depicted in FIG. 11A, in that dual dividing wall columns 600 and 610 in FIG. 11B are both configured to remove three side streams, with the distribution of LAO product fractions being adjusted accordingly. In the configuration depicted in FIG. 11B, dual dividing wall column 600 separates $C_8$ LAOs as an overhead stream, $C_{10}$ LAOs as a first side stream, $C_{12}$ LAOs as a second side stream, $C_{14}$ LAOs as a third side stream, and $C_{16+}$ LAOs as a bottoms stream. The bottoms stream comprising $C_{16+}$ LAOs is received by dual dividing wall column 610, which separates $C_{16}$ LAOs as an overhead stream, $C_{18}$ LAOs as a first side stream, $C_{20}$ LAOs as a second side stream, $C_{22}$ LAOs as a third side stream, and $C_{24+}$ LAOs as a bottoms stream. The bottoms stream comprising $C_{24+}$ LAOs is received by distillation column 620, which separates $C_{24}$ LAOs as an overhead stream and $C_{26+}$ LAOs as a bottoms stream. In another variant (not shown) of the configuration shown in FIG. 11B, distillation column 620 may be omitted in some embodiments.

The configuration depicted in FIG. 11C differs from that depicted in FIG. 11A, in that in FIG. 11C, dual dividing wall column 600 is configured to remove three side streams, and dual dividing wall column 610 is configured to remove two side streams. In the configuration depicted in FIG. 11C, dual dividing wall column 600 separates $C_8$ LAOs as an overhead stream, $C_{10}$ LAOs as a first side stream, $C_{12}$ LAOs as a second side stream, $C_{14}$ LAOs as a third side stream, and $C_{16+}$ LAOs as a bottoms stream. The bottoms stream comprising $C_{16+}$ LAOs is received by dual dividing wall column 610, which separates $C_{16}$ LAOs as an overhead stream, $C_{18}$ LAOs as a first side stream, $C_{20}$ LAOs as a second side stream, and $C_{22+}$ LAOs as a bottoms stream. The bottoms stream comprising $C_{22+}$ LAOs is received by distillation column 620, which may separates $C_{22}$-$C_{24}$ LAOs as an overhead stream and $C_{26+}$ LAOs as a bottoms stream; or $C_{22}$ LAOs as an overhead stream and $C_{24+}$ LAOs as a bottoms stream. In another variant (not shown) of the configuration shown in FIG. 11C, distillation column 620 may be omitted in some embodiments.

Accordingly, certain methods for separating LAOs from one another may comprise providing a pre-processed product stream comprising $C_{8+}$ LAOs to a series of distillation columns comprising a first dual dividing wall column and a second dual dividing wall column linked in fluid communication sequence, in which the first dual dividing wall column separates $C_8$ LAOs as an overhead stream, $C_{10}$ LAOs as a first side stream, $C_{12}$ LAOs as a second side stream, $C_{14}$ LAOs as a third side stream, $C_{16}$ LAOs as a fourth side stream, and $C_{18+}$ LAOs as a bottoms stream, and the second dual dividing wall column may separate $C_{18}$ LAOs as an overhead stream, $C_{20}$ LAOs as a first side stream, $C_{22}$ LAOs as a second side stream, and $C_{24+}$ LAOs as a bottoms stream. In such embodiments, the series of distillation columns may further comprise a two-product distillation column linked in direct fluid communication sequence to the second dual dividing wall column, with the two-product distillation column separating $C_{24}$ LAOs as an overhead stream and $C_{26+}$ LAOs as a bottoms stream.

To this point, the methods of the present disclosure have been described with solvent from the LAO synthesis reaction being separated on the same distillation column that removes the $C_6$ LAOs. That is, in such embodiments, the solvent in the embodiments described heretofore may have a boiling point between 1-hexene and 1-octene to facilitate separation of the solvent. It is to be appreciated that higher boiling solvents, such as solvents having a boiling point between 1-octene and 1-decene, may also be used in the methods of the present disclosure as well. If a solvent having a boiling point between that of 1-octene and 1-decene is employed, separation of the solvent may take place in the series of distillation columns, in which at least one of the distillation columns is a dividing wall column. Alternately, if not separated on the same distillation column that separates 1-hexene, a solvent having a boiling point between that of 1-hexene and 1-octene may be separated as the overhead stream from a first distillation column within the series of distillation columns, wherein the first distillation column may be a two-product distillation column or a dividing wall column.

As described hereinafter, FIGS. 12-14 show how several of the previously described distillation configurations may be employed to separate solvent in conjunction with $C_{8+}$ LAOs. It is to be appreciated that the modified distillation configurations shown in FIGS. 12-14 are illustrative of those described previously hereinabove and are also illustrative of the concepts for separating a higher boiling solvent, specifically a solvent having a boiling point between those of 1-octene and 1-decene. Thus, it is to be understood that any of the distillation column configurations described herein may be modified to accommodate separation of higher boiling solvent, particularly a solvent having a boiling point between those of 1-octene and 1-decene. Likewise, any of the distillation column configurations described herein may be modified to accommodate separation of a lower boiling solvent (i.e., a solvent having a boiling point between those of 1-hexene and 1-octene) as the first overhead stream within the distillation section.

FIG. 12 shows a modified LAO separation sequence using the first distillation column configuration from FIG. 3A, in which a solvent is separated downstream from $C_6$ LAOs. As shown in FIG. 12, dividing wall column 200 separates $C_8$ LAOs as an overhead stream, solvent as a side stream, and $C_{10+}$ LAOs as a bottoms stream. The solvent has a boiling point between those of 1-octene and 1-decene. The solvent removed from the side stream may be recycled to the reactor used for synthesizing LAOs via recycled solvent stream 104 (FIG. 1B or 1D). Continuing with FIG. 12, dividing wall column 210 separates $C_{10}$ LAOs as an overhead stream, $C_{12}$ LAOs as a side stream, and $C_{14+}$ LAOs as a bottoms stream, and dividing wall column 220 separates $C_{14}$ LAOs as an overhead stream, $C_{16}$ LAOs as a side stream, and $C_{18+}$ LAOs as a bottoms stream. Distillation column 230 then may separate $C_{18}$ LAOs as an overhead stream and $C_{20+}$ LAOs as a bottoms stream.

FIG. 13 shows a modified LAO separation sequence using the second distillation column configuration from FIG. 6, in which a solvent is separated downstream from $C_6$ LAOs. As shown in FIG. 13, two-product distillation column 301 separates $C_8$-$C_{10}$ LAOs and solvent as an overhead stream and $C_{12+}$ LAOs as a bottoms stream. The overhead stream from two-product distillation column 301 is passed to dividing wall column 310, which separates $C_8$ LAOs as an overhead stream, solvent as a side stream, and $C_{10}$ LAOs as a bottoms stream. The solvent has a boiling point between those of 1-octene and 1-decene. The solvent removed as the side stream may be recycled to the reactor used for synthesizing LAOs via recycled solvent stream 104 (FIG. 1B or 1D). Continuing with FIG. 13, dividing wall column 320 receives the bottoms stream from two-product distillation column 301 and separates $C_{12}$ LAOs as an overhead stream, $C_{14}$ LAOs as a side stream, and $C_{16+}$ LAOs as a bottoms stream, and dividing wall column 330 separates $C_{16}$ LAOs as an overhead stream, $C_{18}$ LAOs as a side stream, and $C_{20+}$ LAOs as a bottoms stream. Two-product distillation column 341 then may separate $C_{20}$ LAOs as an overhead stream and $C_{22+}$ LAOs as a bottoms stream; $C_{20}$-$C_{22}$ LAOs as an overhead stream and $C_{24+}$ LAOs as a bottoms stream; or $C_{20}$-$C_{24}$ LAOs as an overhead stream and $C_{26+}$ LAOs as a bottoms stream.

FIG. 14 shows a modified LAO separation sequence using the fourth distillation column configuration from FIG. 9, in which a solvent is separated downstream from $C_6$ LAOs. As shown in FIG. 14, dividing wall column 500 separates $C_8$ LAOs as an overhead stream, solvent as a side stream, and $C_{10+}$ LAOs as a bottoms stream. The solvent has a boiling point between those of 1-octene and 1-decene. The solvent removed as the side stream may be recycled to the reactor used for synthesizing LAOs via recycled solvent stream 104 (FIG. 1B or 1D). Continuing with FIG. 14, dual dividing wall column 510 receives the bottoms stream from divided wall column 500 and separates $C_{10}$ LAOs as an overhead stream, $C_{12}$ LAOs as a first side stream, $C_{14}$ LAOs as a second side stream, $C_{16}$ LAOs as a third side stream, $C_{18}$ LAOs as a fourth side stream, and $C_{20+}$ LAOs as a bottoms stream. Distillation column 520 receives the bottoms stream from dual dividing wall column 510 and may separate $C_{20}$-$C_{24}$ LAOs as an overhead stream and $C_{26+}$ LAOs as a bottoms stream; $C_{20}$-$C_{22}$ LAOs as an overhead stream and $C_{24+}$ LAOs as a bottoms stream; or $C_{20}$-$C_{24}$ LAOs as an overhead stream and $C_{26+}$ LAOs as a bottoms stream. It is to be appreciated that dual dividing wall column 510 may be configured to separate a different number of side streams, with the LAO product distribution between dual dividing wall column 510 and distillation column 520 varying accordingly.

Embodiments disclosed herein include: A. Methods for separating LAOs using at least one dividing wall column. The methods comprise: providing a pre-processed product stream comprising $C_{8+}$ linear alpha olefins (LAOs) to a first of a series of distillation columns, at least one member of the series of distillation columns comprising a dividing wall column; and separating an overhead stream comprising a first LAO from the dividing wall column and one or more side streams from the dividing wall column, each side stream comprising a different LAO that also differs from the first LAO.

Embodiment A may have one or more of the following additional elements in any combination:

Element 1: providing a light olefin-depleted product stream comprising $C_{6+}$ LAOs and a solvent to a first distillation column upstream from the series of distillation columns; and separating $C_6$ LAOs as an overhead stream from the first distillation column and $C_{8+}$ LAOs as a bottoms stream from the first distillation column, the bottoms stream being provided as the pre-processed product stream to the series of distillation columns.

Element 2: wherein the method further comprises: separating the solvent as a side stream from the first distillation column.

Element 3: wherein the method further comprises: separating residual ethylene and $C_4$ LAOs from a light olefin-containing product stream using a lead dividing wall column to provide the light olefin-depleted product stream comprising $C_{6+}$ LAOs.

Element 4: wherein the series of distillation columns comprises at least one two-product distillation column at a terminus of the series.

Element 5: wherein the series of distillation columns comprises a sufficient number of distillation columns to separate at different locations $C_8$-$C_{20}$ LAOs having an even carbon count, either as an overhead stream or as a side stream.

Element 6: wherein the series of distillation columns comprises three dividing wall columns linked in direct fluid communication sequence and an additional distillation column at a terminus of the series, the additional distillation column being a two-product distillation column or a dividing wall column.

Element 7: wherein the pre-processed product stream comprising $C_{8+}$ LAOs is provided to a first of the three dividing wall columns; wherein the first of the three dividing wall columns separates $C_8$ LAOs as an overhead stream, $C_{10}$ LAOs as a side stream, and $C_{12+}$ LAOs as a bottoms stream; a second of the three dividing wall columns separates $C_{12}$ LAOs as an overhead stream, $C_{14}$ LAOs as a side stream, and $C_{16+}$ LAOs as a bottoms stream; and a third of the three dividing wall columns separates $C_{16}$ LAOs as an overhead stream, $C_{18}$ LAOs as a side stream, and $C_{20+}$ LAOs as a bottoms stream; or the first of the three dividing wall columns separates $C_8$ LAOs as an overhead stream, $C_{10}$ LAOs as a side stream, and $C_{12+}$ LAOs as a bottoms stream; the second of the three dividing wall columns separates $C_{12}$ LAOs as an overhead stream, $C_{14}$ LAOs as a side stream, and $C_{16+}$ LAOs as a bottoms stream; and the third of the three dividing wall columns separates $C_{16}$ and $C_{18}$ LAOs as an overhead stream, $C_{20}$ LAOs as a side stream, and $C_{22+}$ LAOs as a bottoms stream.

Element 8: wherein the additional distillation column is a two-product distillation column, and the additional distillation column separates $C_{20}$ LAOs as an overhead stream and $C_{22+}$ LAOs as a bottoms stream; $C_{20}$-$C_{22}$ LAOs as an overhead stream and $C_{24+}$ LAOs as a bottoms stream; or $C_{20}$-$C_{24}$ LAOs as an overhead stream and $C_{26+}$ LAOs as a bottoms stream.

Element 9: wherein the additional distillation column is a dividing wall column, and the additional distillation column separates $C_{20}$ LAOs as an overhead stream, $C_{22}$ LAOs as a side stream, and $C_{24+}$ LAOs as a bottoms stream; or $C_{20}$ LAOs as an overhead stream, $C_{22}$-$C_{24}$ LAOs as a side stream, and $C_{26+}$ LAOs as a bottoms stream.

Element 10: wherein the series of distillation columns comprises a two-product distillation column linked in direct fluid communication sequence to a first dividing wall column and a second dividing wall column, and a third dividing wall column linked in direct fluid communication sequence to the second dividing wall column; wherein the first dividing wall column is arranged to receive an overhead stream from the two-product distillation column, the second dividing wall column is arranged to receive a bottoms stream from the two-product distillation column, and the third dividing wall column is arranged to receive a bottoms stream from the second dividing wall column.

Element 11: wherein the pre-processed product stream comprising $C_{8+}$ LAOs is provided to the two-product distillation column; the two-product distillation column separates $C_8$-$C_{12}$ LAOs as an overhead stream and $C_{14+}$ LAOs as a bottoms stream; the first dividing wall column separates $C_8$ LAOs as an overhead stream, $C_{10}$ LAOs as a side stream, and $C_{12}$ LAOs as a bottoms stream; and the second dividing wall column separates $C_{14}$ LAOs as an overhead stream, $C_{16}$ LAOs as a side stream, and $C_{18+}$ LAOs as a bottoms stream.

Element 12: wherein the third dividing wall column separates $C_{18}$ LAOs as an overhead stream, $C_{20-24}$ LAOs as a side stream, and $C_{26+}$ LAOs as a bottoms stream; $C_{18}$ LAOs as an overhead stream, $C_{20-22}$ LAOs as a side stream, and $C_{24+}$ LAOs as a bottoms stream; or $C_{18}$ LAOs as an overhead stream, $C_{20}$ LAOs as a side stream, and $C_{22+}$ LAOs as a bottoms stream.

Element 13: wherein the series of distillation columns further comprises a fourth dividing wall column linked in direct fluid communication sequence to the third dividing wall column, the fourth dividing wall column being arranged to receive a bottoms stream from the third dividing wall column; and wherein the third dividing wall column separates $C_{18}$ LAOs as an overhead stream, $C_{20}$ LAOs as a side stream, and $C_{22+}$ LAOs as a bottoms stream; and the fifth dividing wall column separates $C_{22}$ LAOs as an overhead stream, $C_{24}$ LAOs as a side stream, and $C_{26+}$ LAOs as a bottoms stream.

Element 14: wherein the series of distillation columns further comprises a second two-product distillation column linked in direct fluid communication sequence to the third dividing wall column, the second two-product distillation column being arranged to receive a bottoms stream from the third dividing wall column.

Element 15: wherein the third dividing wall column separates $C_{18}$ LAOs as an overhead stream, $C_{20}$ LAOs as a side stream, and $C_{22+}$ LAOs as a bottoms stream; and the second two-product distillation column separates $C_{22}$ LAOs as an overhead stream and $C_{24+}$ LAOs as a bottoms stream; or $C_{22}$-$C_{24}$ LAOs as an overhead stream and $C_{26+}$ LAOs.

Element 16: wherein the series of distillation columns comprises a first two-product distillation column linked in direct fluid communication sequence to a first dividing wall column and a second dividing wall column, a second two-product distillation column linked in direct fluid communication sequence to the second dividing wall column, and a third two-product distillation column linked in direct fluid communication sequence to the first two-product distillation column; wherein the first dividing wall column is arranged to receive an overhead stream from the first two-product distillation column, the second dividing wall column is arranged to receive a bottoms stream from the first two-product distillation column, the second two-product distillation column is arranged to receive a bottoms stream from the second dividing wall column, and the third two-product distillation column is arranged to receive a bottoms stream from the second two-product distillation column.

Element 17: wherein the pre-processed product stream comprising $C_{8+}$ LAOs is provided to the first two-product distillation column; the first two-product distillation column separates $C_8$-$C_{12}$ LAOs as an overhead stream and $C_{14+}$ LAOs as a bottoms stream; the first dividing wall column separates $C_8$ LAOs as an overhead stream, $C_{10}$ LAOs as a side stream, and $C_{12}$ LAOs as a bottoms stream; the second dividing wall column separates $C_{14}$ LAOs as an overhead stream, $C_{16}$ LAOs as a side stream, and $C_{18+}$ LAOs as a bottoms stream; the second two-product distillation column separates $C_{18}$ LAOs as an overhead stream and $C_{20+}$ LAOs as a bottoms stream; and the third two-product distillation column separates $C_{20}$-$C_{24}$ LAOs as an overhead stream and $C_{26+}$ LAOs as a bottoms stream; $C_{20}$-$C_{22}$ LAOs as an overhead stream and $C_{24+}$ LAOs as a bottoms stream; or $C_{20}$ LAOs as an overhead stream and $C_{22+}$ LAOs as a bottoms stream.

Element 18: wherein the series of distillation columns comprises at least one dividing wall column that is a dual dividing wall column.

Element 19: wherein a first of the series of distillation columns comprises a dual dividing wall column and a second of the series of distillation columns comprises a dividing wall column, the dual dividing wall column and the dividing wall column being linked in direct fluid communication sequence.

Element 20: wherein the pre-processed product stream comprising $C_{8+}$ LAOs is provided to the dual dividing wall column; the dual dividing wall column separates $C_8$ LAOs as an overhead stream, $C_{10}$ LAOs as a first side stream, $C_{12}$ LAOs as a second side stream, $C_{14}$ LAOs as a third side stream, $C_{16}$ LAOs as a fourth side stream, and $C_{18+}$ LAOs as a bottoms stream; and the dividing wall column separates $C_{18}$ LAOs as an overhead stream, $C_{20}$ LAOs as a side stream, and $C_{22+}$ LAOs as a bottoms stream; $C_{18}$ LAOs as an overhead stream, $C_{20}$-$C_{22}$ LAOs as a side stream and $C_{24+}$ LAOs as a bottoms stream; or $C_{18}$ LAOs as an overhead stream, $C_{20}$-$C_{24}$ LAOs as a side stream, and $C_{26+}$ LAOs as a bottoms stream.

Element 21: wherein a first of the series of distillation columns comprises a dividing wall column and a second of the series of distillation columns comprises a dual dividing wall column, the dividing wall column and the dual dividing wall column being linked in direct fluid communication sequence.

Element 22: wherein the pre-processed product stream comprising $C_{8+}$ LAOs is provided to the dividing wall column; the dividing wall column separates $C_8$ LAOs as an overhead stream, $C_{10}$ LAOs as a side stream, and $C_{12+}$ LAOs as a bottoms stream; and the dual dividing wall column separates $C_{12}$ LAOs as an overhead stream, $C_{14}$ LAOs as a first side stream, $C_{16}$ LAOs as a second side stream, $C_{18}$ LAOs as a third side stream, and $C_{20+}$ LAOs as a bottoms stream.

Element 23: wherein the series of distillation columns further comprises a two-product distillation column linked in direct fluid communication sequence to the dual dividing wall column; wherein the two-product distillation column separates $C_{20}$ LAOs as an overhead stream and $C_{22+}$ LAOs as a bottoms stream; $C_{20}$-$C_{22}$ LAOs as an overhead stream and $C_{24+}$ LAOs as a bottoms stream; or $C_{20}$-$C_{24}$ LAOs as an overhead stream and $C_{26+}$ LAOs as a bottoms stream.

Element 24: wherein the pre-processed product stream comprising $C_{8+}$ LAOs is provided to the dividing wall column; the dividing wall column separates $C_8$ LAOs as an overhead stream, $C_{10}$ LAOs as a side stream, and $C_{12+}$ LAOs as a bottoms stream; and the dual dividing wall column separates $C_{12}$ LAOs as an overhead stream, $C_{14}$ LAOs as a first side stream, $C_{16}$ LAOs as a second side stream, $C_{18}$ LAOs as a third side stream, $C_{20}$ LAOs as a fourth side stream, and $C_{22+}$ LAOs as a bottoms stream.

Element 25: wherein the series of distillation columns further comprises a two-product distillation column linked in direct fluid communication sequence to the dual dividing wall column; wherein the two-product distillation column separates $C_{22}$ LAOs as an overhead stream and $C_{24+}$ LAOs as a bottoms stream, or $C_{22}$-$C_{24}$ LAOs as an overhead stream and $C_{26+}$ LAOs as a bottoms stream.

Element 26: wherein the series of distillation columns comprises two dual dividing wall columns linked in direct fluid communication, a first member of the series of distillation columns comprising a first dual dividing wall column and a second member of the series of distillation columns comprising a second dual dividing wall column.

Element 27: wherein the pre-processed product stream comprising $C_{8+}$ LAOs is provided to the first dual dividing wall column; the first dual dividing wall column separates $C_8$ LAOs as an overhead stream, $C_{10}$ LAOs as a first side stream, $C_{12}$ LAOs as a second side stream, $C_{14}$ LAOs as a third side stream, $C_{16}$ LAOs as a fourth side stream, and $C_{18+}$ LAOs as a bottoms stream; and the second dual dividing wall column separates $C_{18}$ LAOs as an overhead stream, $C_{20}$ LAOs as a first side stream, $C_{22}$ LAOs as a second side stream, and $C_{24+}$ LAOs as a bottoms stream.

Element 28: wherein the series of distillation columns further comprises a two-product distillation column linked in direct fluid communication sequence to the second dual dividing wall column; and the two-product distillation column separates $C_{24}$ LAOs an overhead stream and $C_{26+}$ LAOs as a bottoms stream.

Element 29: wherein the pre-processed product stream is obtained from a product stream formed through oligomerization of ethylene in the presence of a Ziegler-type catalyst.

By way of non-limiting example, exemplary combinations include: The method of A in combination with elements 1 and 4; 1, 2 and 4; 4 and 6; 6 and 7; 6-8; 6, 7 and 9; 1 and 5; 1, 2 and 5; 5 and 6; 1 and 6; 1, 2 and 6; 1 and 10; 1, 2 and 10; 10 and 11; 10-12; 10, 11 and 13; 10, 11 and 14; 10, 11, 14 and 15; 1 and 16; 1, 2 and 16; 16 and 17; 1 and 18; 1, 2 and 18; 18 and 19; 18-20; 18 and 21; 18, 21 and 22; 18, 21 and 23; 18, 21 and 24; 18, 21 and 25; 18, 24 and 25; 18 and 26; 18, 26 and 27; and 18 and 26-28, any of which may be in further combination with element 29. The method of A in combination with elements 1 and 29; 4 and 29; 5 and 29; 6 and 29; 10 and 29; 11 and 29; 16 and 29; and 18 and 29.

All documents described herein are incorporated by reference herein for purposes of all jurisdictions where such practice is allowed, including any priority documents and/or testing procedures to the extent they are not inconsistent with this text. As is apparent from the foregoing general description and the specific embodiments, while forms of the disclosure have been illustrated and described, various modifications can be made without departing from the spirit and scope of the disclosure. Accordingly, it is not intended that the disclosure be limited thereby. For example, the compositions described herein may be free of any component, or composition not expressly recited or disclosed herein. Any method may lack any step not recited or disclosed herein. Likewise, the term "comprising" is considered synonymous with the term "including." Whenever a method, composition, element or group of elements is preceded with the transitional phrase "comprising," it is understood that we also contemplate the same composition or group of elements with transitional phrases "consisting essentially of," "consisting of," "selected from the group of consisting of," or "is" preceding the recitation of the composition, element, or elements and vice versa.

Unless otherwise indicated, all numbers expressing quantities of ingredients, properties such as molecular weight, reaction conditions, and so forth used in the present specification and associated claims are to be understood as being modified in all instances by the term "about." Accordingly, unless indicated to the contrary, the numerical parameters set forth in the following specification and attached claims are approximations that may vary depending upon the desired properties sought to be obtained by the embodiments of the present invention. At the very least, and not as an attempt to limit the application of the doctrine of equivalents to the scope of the claim, each numerical parameter should at least be construed in light of the number of reported significant digits and by applying ordinary rounding techniques.

Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the element that it introduces.

One or more illustrative embodiments are presented herein. Not all features of a physical implementation are described or shown in this application for the sake of clarity. It is understood that in the development of a physical embodiment of the present disclosure, numerous implementation-specific decisions must be made to achieve the developer's goals, such as compliance with system-related, business-related, government-related and other constraints, which vary by implementation and from time to time. While a developer's efforts might be time-consuming, such efforts would be, nevertheless, a routine undertaking for one of ordinary skill in the art and having benefit of this disclosure.

Therefore, the present disclosure is well adapted to attain the ends and advantages mentioned as well as those that are inherent therein. The particular embodiments disclosed above are illustrative only, as the present disclosure may be modified and practiced in different but equivalent manners apparent to one having ordinary skill in the art and having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope and spirit of the present disclosure. The embodiments illustratively disclosed herein suitably may be practiced in the absence of any element that is not specifically disclosed herein and/or any optional element disclosed herein.

What is claimed is:

1. A method comprising:
providing a pre-processed product stream comprising $C_{8+}$ linear alpha olefins (LAOs) to a first of a series of distillation columns, at least one member of the series of distillation columns comprising a dividing wall column;
providing a light olefin-depleted product stream comprising $C_{6+}$ LAOs and a solvent to a first distillation column upstream from the series of distillation columns;
separating $C_6$ LAOs as an overhead stream from the first distillation column and $C_{8+}$ LAOs as a bottoms stream from the first distillation column, the bottoms stream being the pre-processed product stream provided to the series of distillation columns; and separating an overhead stream comprising a first LAO from the dividing wall column and one or more side streams from the dividing wall column, each side stream comprising a different LAO that also differs from the first LAO.

2. The method of claim 1, further comprising:
separating the solvent as a side stream from the first distillation column.

3. The method of claim 1, further comprising:
separating residual ethylene and $C_4$ LAOs from a light olefin-containing product stream using a lead dividing wall column to provide the light olefin-depleted product stream comprising $C_{6+}$ LAOs.

4. The method of claim 1, wherein the series of distillation columns comprises at least one two-product distillation column at a terminus of the series.

5. The method of claim 1, wherein the series of distillation columns comprises at least one two-product distillation column and at least one divided wall distillation column to separate at different locations $C_8$-$C_{20}$ LAOs having an even carbon count, either as an overhead stream or as a side stream.

6. The method of claim 1, wherein the series of distillation columns comprises three dividing wall columns linked in direct fluid communication sequence and an additional distillation column at a terminus of the series, the additional distillation column being a two-product distillation column or a dividing wall column.

7. The method of claim 6, wherein the pre-processed product stream comprising $C_{8+}$ LAOs is provided to a first of the three dividing wall columns;
wherein the first of the three dividing wall columns separates $C_8$ LAOs as an overhead stream, $C_{10}$ LAOs as a side stream, and $C_{12+}$ LAOs as a bottoms stream; a second of the three dividing wall columns separates $C_{12}$ LAOs as an overhead stream, $C_{14}$ LAOs as a side stream, and $C_{16+}$ LAOs as a bottoms stream; and a third of the three dividing wall columns separates $C_{16}$ LAOs as an overhead stream, $C_{18}$ LAOs as a side stream, and $C_{20+}$ LAOs as a bottoms stream; or the first of the three dividing wall columns separates $C_8$ LAOs as an overhead stream, $C_{10}$ LAOs as a side stream, and $C_{12+}$ LAOs as a bottoms stream; the second of the three dividing wall columns separates $C_{12}$ LAOs as an overhead stream, $C_{14}$ LAOs as a side stream, and $C_{16+}$ LAOs as a bottoms stream; and the third of the three dividing wall columns separates $C_{16}$ and $C_{18}$ LAOs as an overhead stream, $C_{20}$ LAOs as a side stream, and $C_{22+}$ LAOs as a bottoms stream.

8. The method of claim 7, wherein the additional distillation column is a two-product distillation column, and the additional distillation column separates $C_{20}$ LAOs as an overhead stream and $C_{22+}$ LAOs as a bottoms stream; $C_{20}$-$C_{22}$ LAOs as an overhead stream and $C_{24+}$ LAOs as a bottoms stream; or $C_{20}$-$C_{24}$ LAOs as an overhead stream and $C_{26+}$ LAOs as a bottoms stream.

9. The method of claim 7, wherein the additional distillation column is a dividing wall column, and the additional distillation column separates $C_{20}$ LAOs as an overhead stream, $C_{22}$ LAOs as a side stream, and $C_{24+}$ LAOs as a bottoms stream; or $C_{20}$ LAOs as an overhead stream, $C_{22}$-$C_{24}$ LAOs as a side stream, and $C_{26+}$ LAOs as a bottoms stream.

10. The method of claim 1, wherein the series of distillation columns comprises a two-product distillation column linked in direct fluid communication sequence to a first dividing wall column and a second dividing wall column, and a third dividing wall column linked in direct fluid communication sequence to the second dividing wall column;
wherein the first dividing wall column is arranged to receive an overhead stream from the two-product distillation column, the second dividing wall column is arranged to receive a bottoms stream from the two-product distillation column, and the third dividing wall column is arranged to receive a bottoms stream from the second dividing wall column.

11. The method of claim 10, wherein the pre-processed product stream comprising $C_{8+}$ LAOs is provided to the two-product distillation column; the two-product distillation column separates $C_8$-$C_{12}$ LAOs as an overhead stream and $C_{14+}$ LAOs as a bottoms stream; the first dividing wall column separates $C_8$ LAOs as an overhead stream, $C_{10}$ LAOs as a side stream, and $C_{12}$ LAOs as a bottoms stream; and the second dividing wall column separates $C_{14}$ LAOs as an overhead stream, $C_{16}$ LAOs as a side stream, and $C_{18+}$ LAOs as a bottoms stream.

12. The method of claim 11, wherein the third dividing wall column separates $C_{18}$ LAOs as an overhead stream, $C_{20-24}$ LAOs as a side stream, and $C_{26+}$ LAOs as a bottoms stream; $C_{18}$ LAOs as an overhead stream, $C_{20-22}$ LAOs as a side stream, and $C_{24+}$ LAOs as a bottoms stream; or $C_{18}$ LAOs as an overhead stream, $C_{20}$ LAOs as a side stream, and $C_{22+}$ LAOs as a bottoms stream.

13. The method of claim 11, wherein the series of distillation columns further comprises a fourth dividing wall column linked in direct fluid communication sequence to the third dividing wall column, the fourth dividing wall column being arranged to receive a bottoms stream from the third dividing wall column; and
wherein the third dividing wall column separates $C_{18}$ LAOs as an overhead stream, $C_{20}$ LAOs as a side stream, and $C_{22+}$ LAOs as a bottoms stream; and the fifth dividing wall column separates $C_{22}$ LAOs as an overhead stream, $C_{24}$ LAOs as a side stream, and $C_{26+}$ LAOs as a bottoms stream.

14. The method of claim 11, wherein the series of distillation columns further comprises a second two-product distillation column linked in direct fluid communication sequence to the third dividing wall column, the second two-product distillation column being arranged to receive a bottoms stream from the third dividing wall column.

15. The method of claim 14, wherein the third dividing wall column separates $C_{18}$ LAOs as an overhead stream, $C_{20}$ LAOs as a side stream, and $C_{22+}$ LAOs as a bottoms stream; and the second two-product distillation column separates $C_{22}$ LAOs as an overhead stream and $C_{24+}$ LAOs as a bottoms stream; or $C_{22}$-$C_{24}$ LAOs as an overhead stream and $C_{26+}$ LAOs.

16. The method of claim 1, wherein the series of distillation columns comprises a first two-product distillation column linked in direct fluid communication sequence to a first dividing wall column and a second dividing wall column, a second two-product distillation column linked in direct fluid communication sequence to the second dividing wall column, and a third two-product distillation column linked in direct fluid communication sequence to the first two-product distillation column;
wherein the first dividing wall column is arranged to receive an overhead stream from the first two-product distillation column, the second dividing wall column is arranged to receive a bottoms stream from the first two-product distillation column, the second two-product distillation column is arranged to receive a bottoms stream from the second dividing wall column, and the third two-product distillation column is arranged to receive a bottoms stream from the second two-product distillation column.

17. The method of claim 16, wherein the pre-processed product stream comprising $C_{8+}$ LAOs is provided to the first two-product distillation column; the first two-product distillation column separates $C_8$-$C_{12}$ LAOs as an overhead stream and $C_{14+}$ LAOs as a bottoms stream; the first dividing wall column separates $C_8$ LAOs as an overhead stream, $C_{10}$ LAOs as a side stream, and $C_{12}$ LAOs as a bottoms stream; the second dividing wall column separates $C_{14}$ LAOs as an overhead stream, $C_{16}$ LAOs as a side stream, and $C_{18+}$ LAOs as a bottoms stream; the second two-product distillation column separates $C_{18}$ LAOs as an overhead stream and $C_{20+}$ LAOs as a bottoms stream; and the third two-product distillation column separates $C_{20}$-$C_{24}$ LAOs as an overhead stream and $C_{26+}$ LAOs as a bottoms stream; $C_{20}$-$C_{22}$ LAOs as an overhead stream and $C_{24+}$ LAOs as a bottoms stream; or $C_{20}$ LAOs as an overhead stream and $C_{22+}$ LAOs as a bottoms stream.

18. The method of claim 1, wherein the series of distillation columns comprises at least one dividing wall column that is a dual dividing wall column.

19. The method of claim 18, wherein a first of the series of distillation columns comprises a dual dividing wall column and a second of the series of distillation columns comprises a dividing wall column, the dual dividing wall column and the dividing wall column being linked in direct fluid communication sequence.

20. The method of claim 19, wherein the pre-processed product stream comprising $C_{8+}$ LAOs is provided to the dual dividing wall column; the dual dividing wall column separates $C_8$ LAOs as an overhead stream, $C_{10}$ LAOs as a first side stream, $C_{12}$ LAOs as a second side stream, $C_{14}$ LAOs as a third side stream, $C_{16}$ LAOs as a fourth side stream, and $C_{18+}$ LAOs as a bottoms stream; and the dividing wall column separates $C_{18}$ LAOs as an overhead stream, $C_{20}$ LAOs as a side stream, and $C_{22+}$ LAOs as a bottoms stream; $C_{18}$ LAOs as an overhead stream, $C_{20}$-$C_{22}$ LAOs as a side stream and $C_{24+}$ LAOs as a bottoms stream; or $C_{18}$ LAOs as an overhead stream, $C_{20}$-$C_{24}$ LAOs as a side stream, and $C_{26+}$ LAOs as a bottoms stream.

21. The method of claim 18, wherein a first of the series of distillation columns comprises a dividing wall column and a second of the series of distillation columns comprises a dual dividing wall column, the dividing wall column and the dual dividing wall column being linked in direct fluid communication sequence.

22. The method of claim 21, wherein the pre-processed product stream comprising $C_{8+}$ LAOs is provided to the dividing wall column; the dividing wall column separates $C_8$ LAOs as an overhead stream, $C_{10}$ LAOs as a side stream, and $C_{12+}$ LAOs as a bottoms stream; and the dual dividing wall column separates $C_{12}$ LAOs as an overhead stream, $C_{14}$ LAOs as a first side stream, $C_{16}$ LAOs as a second side stream, $C_{18}$ LAOs as a third side stream, and $C_{20+}$ LAOs as a bottoms stream.

23. The method of claim 21, wherein the series of distillation columns further comprises a two-product distillation column linked in direct fluid communication sequence to the dual dividing wall column;
wherein the two-product distillation column separates $C_{20}$ LAOs as an overhead stream and $C_{22+}$ LAOs as a bottoms stream; $C_{20}$-$C_{22}$ LAOs as an overhead stream and $C_{24+}$ LAOs as a bottoms stream; or $C_{20}$-$C_{24}$ LAOs as an overhead stream and $C_{26+}$ LAOs as a bottoms stream.

24. The method of claim 21, wherein the pre-processed product stream comprising $C_{8+}$ LAOs is provided to the dividing wall column; the dividing wall column separates $C_8$ LAOs as an overhead stream, $C_{10}$ LAOs as a side stream, and $C_{12+}$ LAOs as a bottoms stream; and the dual dividing wall column separates $C_{12}$ LAOs as an overhead stream, $C_{14}$ LAOs as a first side stream, $C_{16}$ LAOs as a second side stream, $C_{18}$ LAOs as a third side stream, $C_{20}$ LAOs as a fourth side stream, and $C_{22+}$ LAOs as a bottoms stream.

25. The method of claim 21, wherein the series of distillation columns further comprises a two-product distillation column linked in direct fluid communication sequence to the dual dividing wall column;
wherein the two-product distillation column separates $C_{22}$ LAOs as an overhead stream and $C_{24+}$ LAOs as a bottoms stream, or $C_{22}$-$C_{24}$ LAOs as an overhead stream and $C_{26+}$ LAOs as a bottoms stream.

26. The method of claim 21, wherein the pre-processed product stream is obtained from a product stream formed through oligomerization of ethylene in the presence of a Ziegler-type catalyst.

27. The method of claim 18, wherein the series of distillation columns comprises two dual dividing wall columns linked in direct fluid communication, a first member of the series of distillation columns comprising a first dual dividing wall column and a second member of the series of distillation columns comprising a second dual dividing wall column.

28. The method of claim 27, wherein the pre-processed product stream comprising $C_{8+}$ LAOs is provided to the first dual dividing wall column; the first dual dividing wall column separates $C_8$ LAOs as an overhead stream, $C_{10}$ LAOs as a first side stream, $C_{12}$ LAOs as a second side stream, $C_{14}$ LAOs as a third side stream, $C_{16}$ LAOs as a fourth side stream, and $C_{18+}$ LAOs as a bottoms stream; and the second dual dividing wall column separates $C_{18}$ LAOs as an overhead stream, $C_{20}$ LAOs as a first side stream, $C_{22}$ LAOs as a second side stream, and $C_{24+}$ LAOs as a bottoms stream.

29. The method of claim 28, wherein the series of distillation columns further comprises a two-product distillation column linked in direct fluid communication sequence to the second dual dividing wall column; and the two-product distillation column separates $C_{24}$ LAOs an overhead stream and $C_{26+}$ LAOs as a bottoms stream.

* * * * *